(12) United States Patent
Kugler et al.

(10) Patent No.: US 10,806,474 B2
(45) Date of Patent: Oct. 20, 2020

(54) SYSTEMS, APPARATUS AND METHODS FOR TREATING BLOOD VESSELS

(71) Applicant: BOSTON SCIENTIFIC SCIMED, INC., Maple Grove, MN (US)

(72) Inventors: Chad J. Kugler, Buffalo, MN (US); David B. Robinson, Chanhassen, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 322 days.

(21) Appl. No.: 15/848,822

(22) Filed: Dec. 20, 2017

(65) Prior Publication Data

US 2018/0110537 A1    Apr. 26, 2018

Related U.S. Application Data

(63) Continuation of application No. 14/205,901, filed on Mar. 12, 2014, now Pat. No. 9,878,128.
(Continued)

(51) Int. Cl.
*A61B 17/225* (2006.01)
*A61B 17/3207* (2006.01)
(Continued)

(52) U.S. Cl.
CPC ...... *A61B 17/2256* (2013.01); *A61B 17/3207* (2013.01); *A61M 25/0194* (2013.01); *A61B 17/12136* (2013.01); *A61B 2017/00477* (2013.01); *A61B 2017/22044* (2013.01); *A61B 2017/22067* (2013.01);
(Continued)

(58) Field of Classification Search
CPC ............... A61F 2/954; A61B 17/12136; A61B 17/2256; A61B 17/3207; A61B 17/3478; A61B 2017/00477; A61B 2017/22044; A61B 2017/22067; A61B 2017/22071; A61B 2017/22095; A61M 25/0194; A61M 2025/0681; A61M 2025/0197
See application file for complete search history.

(56) References Cited

U.S. PATENT DOCUMENTS 4,870,953 A   10/1989   DonMicheal et al.
5,830,222 A   11/1998   Makower
(Continued)

FOREIGN PATENT DOCUMENTS

WO     2013003194 A1    1/2013

*Primary Examiner* — Ashley L Fishback
(74) *Attorney, Agent, or Firm* — Seager, Tufte & Wickhem LLP

(57) ABSTRACT

A system and method for treating a blood vessel that is at least partially obstructed by an occlusion which divides the lumen into a proximal lumen segment and a distal lumen segment. The system includes an orienting catheter having an orientation element positionable in an intrawall space of the vessel and an occlusion catheter having an occlusion balloon inflatable in the proximal lumen segment so as to isolate a target volume including the intrawall space. The pressure inside the target volume is reduced to a pressure below the pressure of the distal lumen segment so that the intima presses against the orienting element of the orienting catheter. A distal end of a reentry device may be advanced from the orienting catheter through the intima and into the distal lumen segment.

18 Claims, 25 Drawing Sheets

Related U.S. Application Data

(60) Provisional application No. 61/781,217, filed on Mar. 14, 2013.

(51) Int. Cl.
*A61M 25/01* (2006.01)
*A61M 25/06* (2006.01)
*A61B 17/12* (2006.01)
*A61B 17/00* (2006.01)
*A61B 17/22* (2006.01)

(52) U.S. Cl.
CPC ............ *A61B 2017/22071* (2013.01); *A61B 2017/22095* (2013.01); *A61M 2025/0197* (2013.01); *A61M 2025/0681* (2013.01)

(56) References Cited

U.S. PATENT DOCUMENTS

| | | |
|---|---|---|
| 5,935,108 A | 8/1999 | Katoh et al. |
| 5,938,671 A | 8/1999 | Katoh et al. |
| 5,968,064 A | 10/1999 | Selmon et al. |
| 6,010,449 A | 1/2000 | Selmon et al. |
| 6,068,638 A | 5/2000 | Makower |
| 6,120,516 A | 9/2000 | Selmon et al. |
| 6,159,225 A | 12/2000 | Makower |
| 6,190,353 B1 | 2/2001 | Makower et al. |
| 6,217,527 B1 | 4/2001 | Selmon et al. |
| 6,217,549 B1 | 4/2001 | Selmon et al. |
| 6,221,049 B1 | 4/2001 | Selmon et al. |
| 6,231,546 B1 | 5/2001 | Milo et al. |
| 6,231,587 B1 | 5/2001 | Makower |
| 6,235,000 B1 | 5/2001 | Milo et al. |
| 6,241,667 B1 | 6/2001 | Vetter et al. |
| 6,398,798 B2 | 6/2002 | Selmon et al. |
| 6,506,178 B1 | 1/2003 | Schubart et al. |
| 6,508,825 B1 | 1/2003 | Selmon et al. |
| 6,511,458 B2 | 1/2003 | Milo et al. |
| 6,514,217 B1 | 2/2003 | Selmon et al. |
| 6,579,302 B2 | 6/2003 | Duerig et al. |
| 6,599,304 B1 | 7/2003 | Selmon et al. |
| 6,638,247 B1 | 10/2003 | Selmon et al. |
| 6,663,577 B2 | 12/2003 | Jen et al. |
| 6,709,444 B1 | 3/2004 | Makower |
| 6,719,725 B2 | 4/2004 | Milo et al. |
| 6,955,175 B2 | 10/2005 | Stevens et al. |
| 7,004,173 B2 | 2/2006 | Sparks et al. |
| 7,179,270 B2 | 2/2007 | Makower |
| 7,229,421 B2 | 6/2007 | Jen et al. |
| 7,357,794 B2 | 4/2008 | Makower et al. |
| 7,740,623 B2 | 6/2010 | Nayak et al. |
| 7,918,859 B2 | 4/2011 | Katoh et al. |
| 7,918,870 B2 | 4/2011 | Kugler et al. |
| 7,938,819 B2 | 5/2011 | Kugler et al. |
| 8,025,655 B2 | 9/2011 | Kugler et al. |
| 8,083,727 B2 | 12/2011 | Kugler et al. |
| 8,202,246 B2 | 6/2012 | Kugler et al. |
| 8,323,261 B2 | 12/2012 | Kugler et al. |
| 8,337,425 B2 | 12/2012 | Olson et al. |
| 8,512,310 B2 | 8/2013 | Kugler et al. |
| 9,278,192 B2* | 3/2016 | Copeta .............. A61M 25/0194 |
| 9,402,981 B2* | 8/2016 | Anderson ........... A61M 25/104 |
| 9,451,984 B2* | 9/2016 | Zhou .................. A61B 17/3207 |
| 9,603,615 B2* | 3/2017 | Sarge ............... A61B 17/22012 |
| 9,878,128 B2 | 1/2018 | Kugler et al. |
| 2001/0000041 A1 | 3/2001 | Selmon et al. |
| 2001/0003161 A1 | 6/2001 | Vardi et al. |
| 2001/0012924 A1 | 8/2001 | Milo et al. |
| 2002/103459 A1 | 8/2002 | Sparks et al. |
| 2002/0128677 A1 | 9/2002 | Duerig et al. |
| 2002/0183763 A1 | 12/2002 | Callol et al. |
| 2003/0023204 A1* | 1/2003 | Vo ........................ A61B 17/12 604/103.07 |
| 2003/0109809 A1 | 6/2003 | Jen et al. |
| 2003/0120195 A1 | 6/2003 | Milo et al. |
| 2003/0139763 A1 | 7/2003 | Duerig et al. |
| 2003/0181923 A1* | 9/2003 | Vardi .................... A61F 2/856 606/108 |
| 2003/0195546 A1 | 10/2003 | Solar et al. |
| 2003/0236542 A1* | 12/2003 | Makower ............. A61B 1/3137 606/167 |
| 2004/0167554 A1 | 8/2004 | Simpson et al. |
| 2004/0230219 A1 | 11/2004 | Roucher, Jr. |
| 2005/0149062 A1 | 7/2005 | Carroll |
| 2005/0171478 A1 | 8/2005 | Selmon et al. |
| 2006/0094930 A1 | 5/2006 | Sparks et al. |
| 2006/0167437 A1 | 7/2006 | Valencia |
| 2006/0184011 A1 | 8/2006 | Macaulay et al. |
| 2006/0276749 A1 | 12/2006 | Selmon et al. |
| 2007/0093779 A1 | 4/2007 | Kugler et al. |
| 2007/0093780 A1* | 4/2007 | Kugler ................. A61B 17/221 604/510 |
| 2007/0093781 A1 | 4/2007 | Kugler et al. |
| 2007/0093782 A1 | 4/2007 | Kugler et al. |
| 2007/0208368 A1 | 9/2007 | Katoh et al. |
| 2007/0219625 A1 | 9/2007 | Venturelli et al. |
| 2007/0265596 A1 | 11/2007 | Jen et al. |
| 2008/0033423 A1 | 2/2008 | Peacock |
| 2008/0125748 A1 | 5/2008 | Patel |
| 2008/0154172 A1 | 6/2008 | Mauch |
| 2008/0200896 A1 | 8/2008 | Shmulewitz et al. |
| 2008/0228171 A1 | 9/2008 | Kugler et al. |
| 2008/0243065 A1 | 10/2008 | Rottenberg et al. |
| 2008/0243067 A1* | 10/2008 | Rottenberg ............ A61B 17/02 604/99.01 |
| 2008/0249397 A1 | 10/2008 | Kapadia |
| 2009/0005755 A1 | 1/2009 | Keith et al. |
| 2009/0088685 A1* | 4/2009 | Kugler ................. A61B 17/221 604/101.01 |
| 2009/0093791 A1 | 4/2009 | Heuser |
| 2009/0124899 A1 | 5/2009 | Jacobs et al. |
| 2009/0209910 A1 | 8/2009 | Kugler et al. |
| 2009/0230167 A1 | 9/2009 | Xiao et al. |
| 2009/0254107 A1* | 10/2009 | Katoh ............... A61M 25/0012 606/159 |
| 2009/0264826 A1* | 10/2009 | Thompson ......... A61B 17/3207 604/164.13 |
| 2009/0292296 A1 | 11/2009 | Pansky et al. |
| 2009/0299171 A1 | 12/2009 | Duffy et al. |
| 2009/0299402 A1 | 12/2009 | Orihashi et al. |
| 2010/0063534 A1* | 3/2010 | Kugler ................. A61B 17/221 606/200 |
| 2010/0069945 A1* | 3/2010 | Olson .................... A61B 17/11 606/185 |
| 2010/0125244 A1 | 5/2010 | McAndrew |
| 2010/0317973 A1* | 12/2010 | Nita .................... A61B 18/1492 600/467 |
| 2011/0112564 A1 | 5/2011 | Wolf |
| 2011/0144677 A1 | 6/2011 | Ward et al. |
| 2011/0166591 A1 | 7/2011 | Katoh et al. |

* cited by examiner

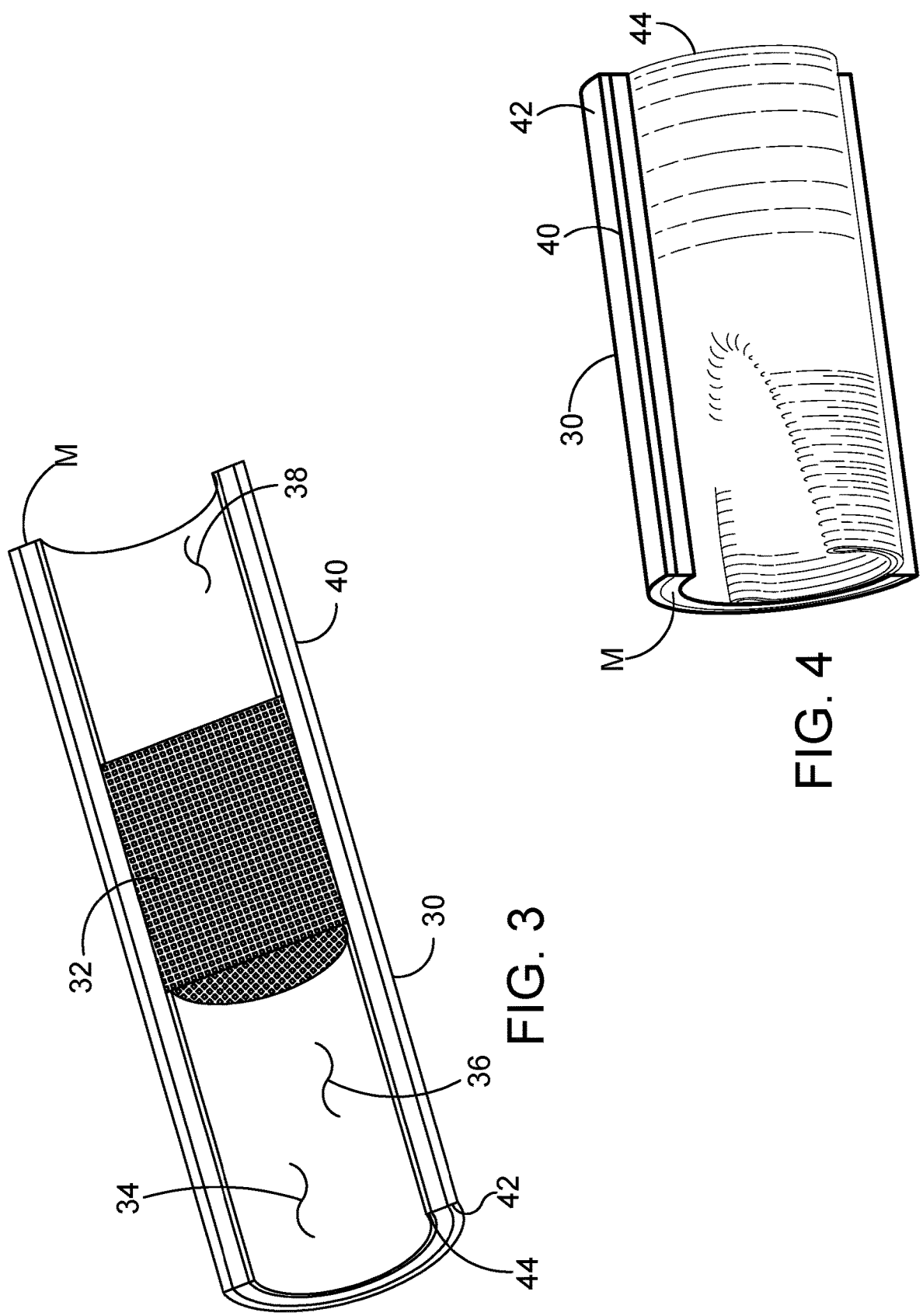

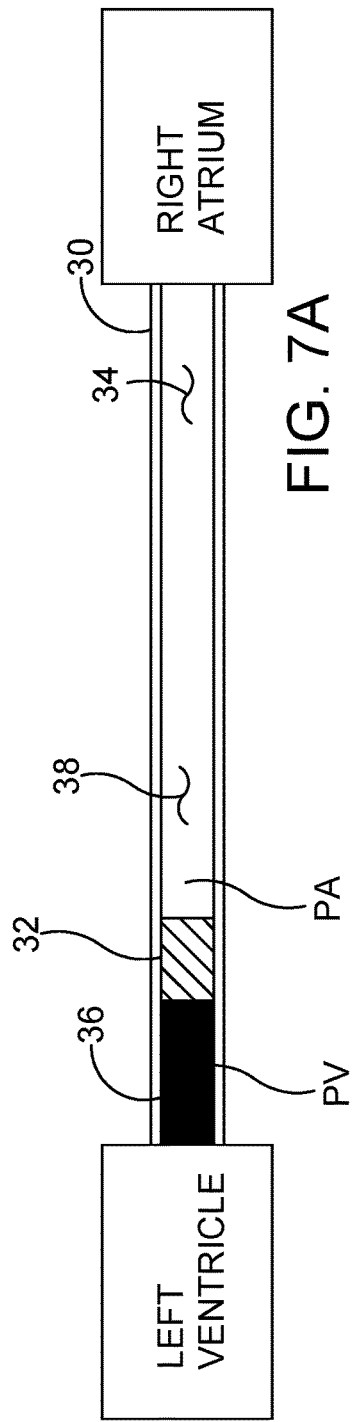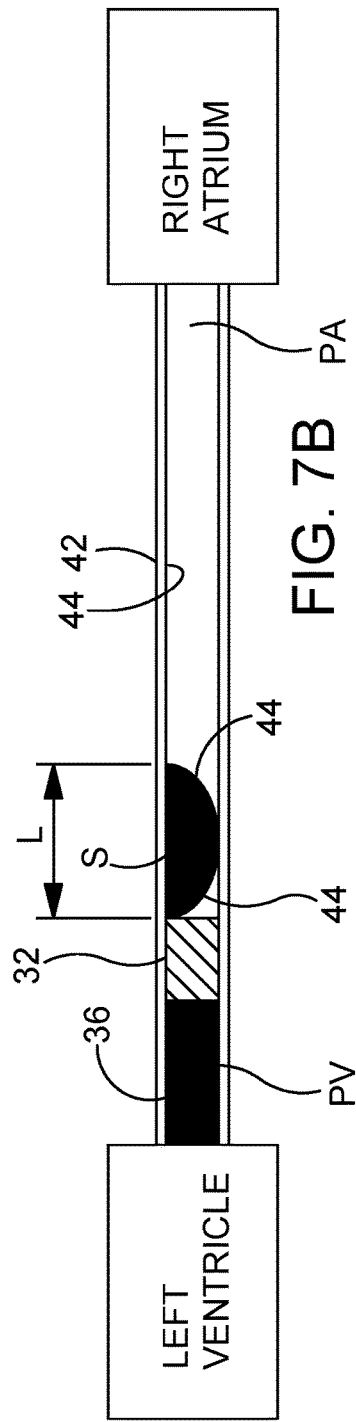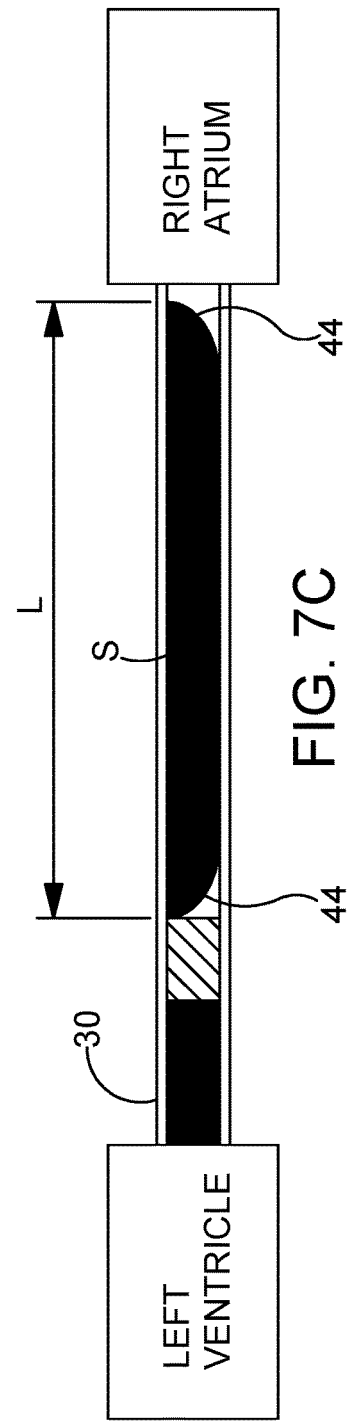

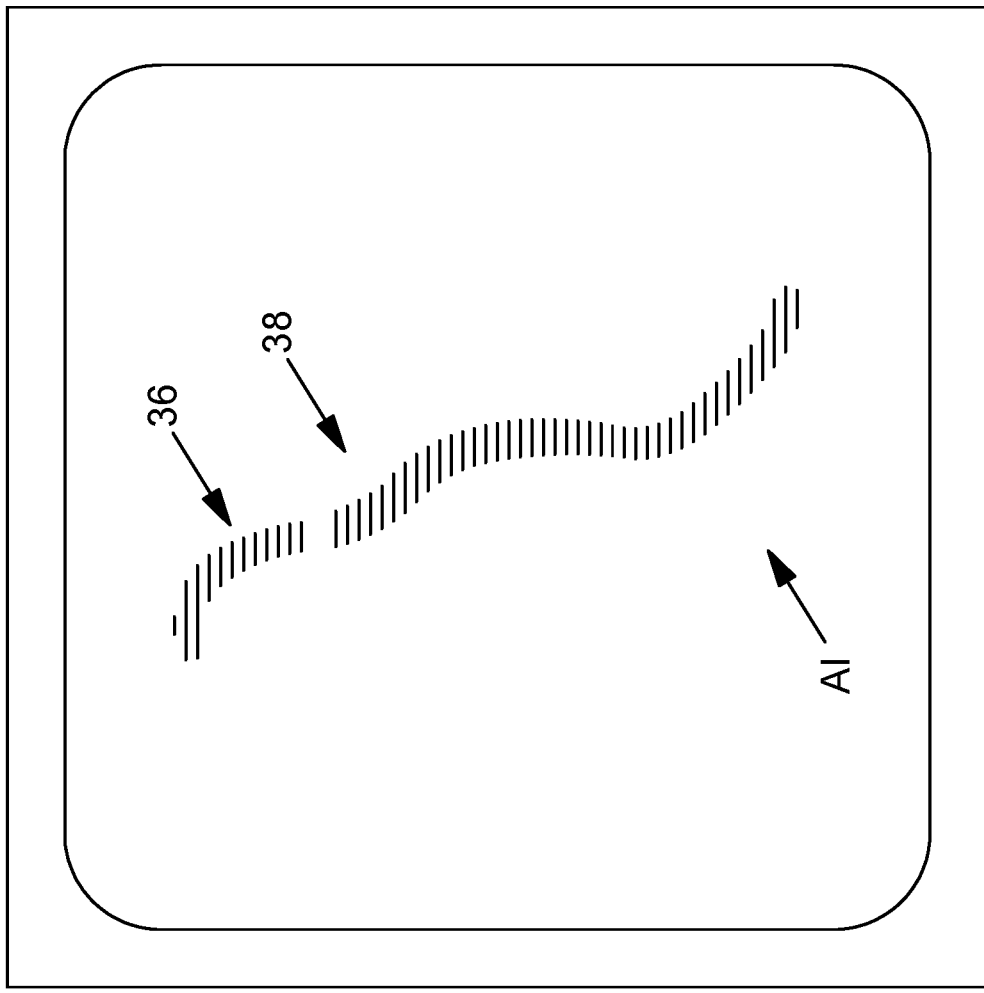
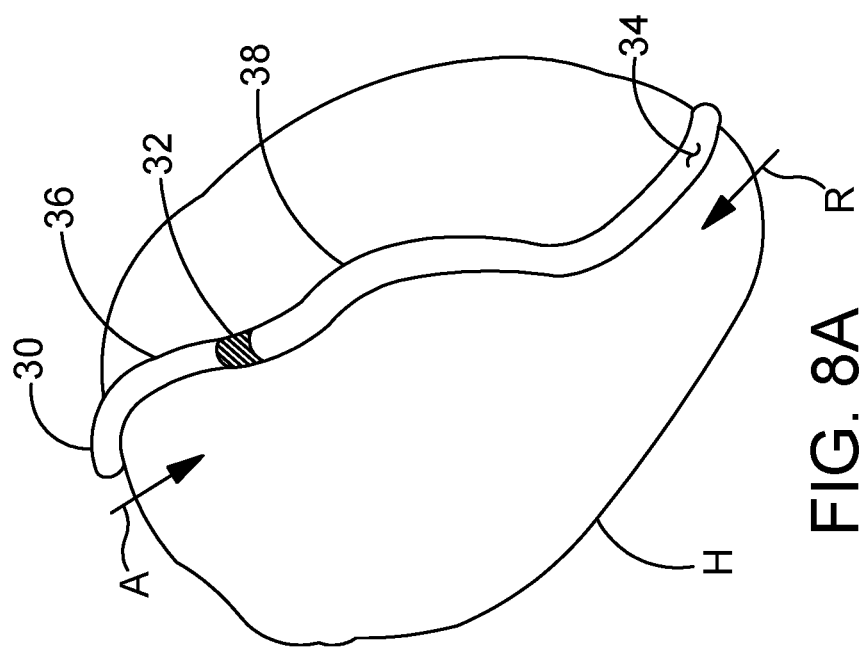

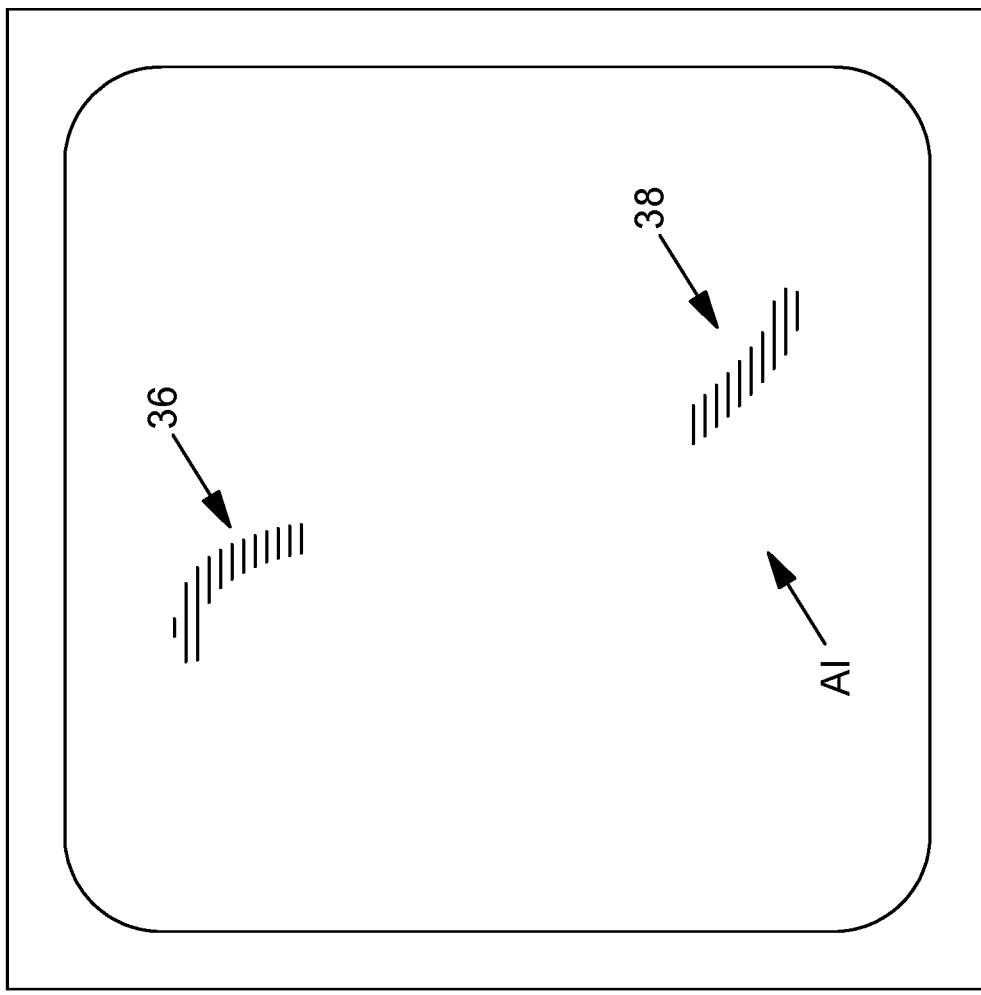
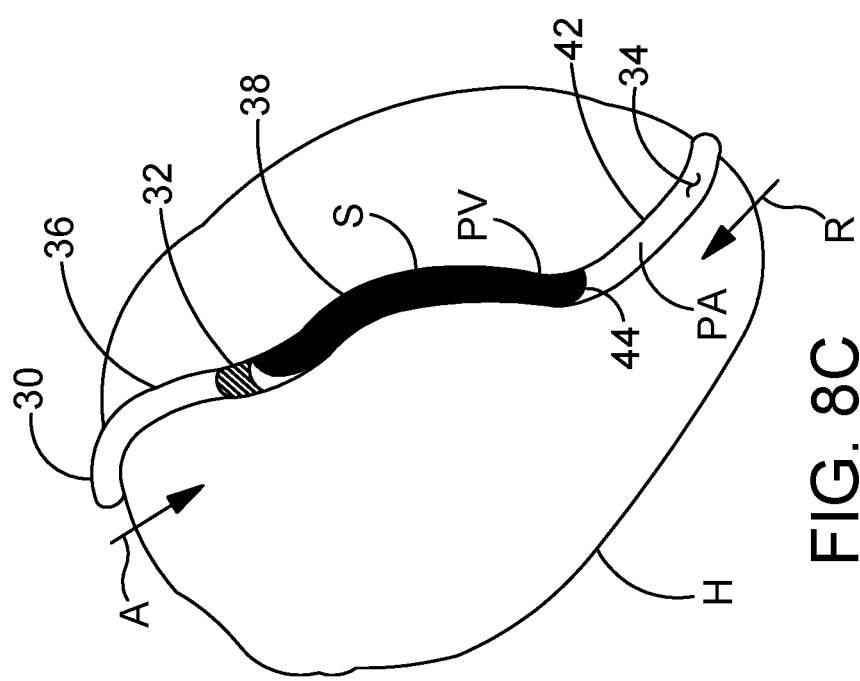

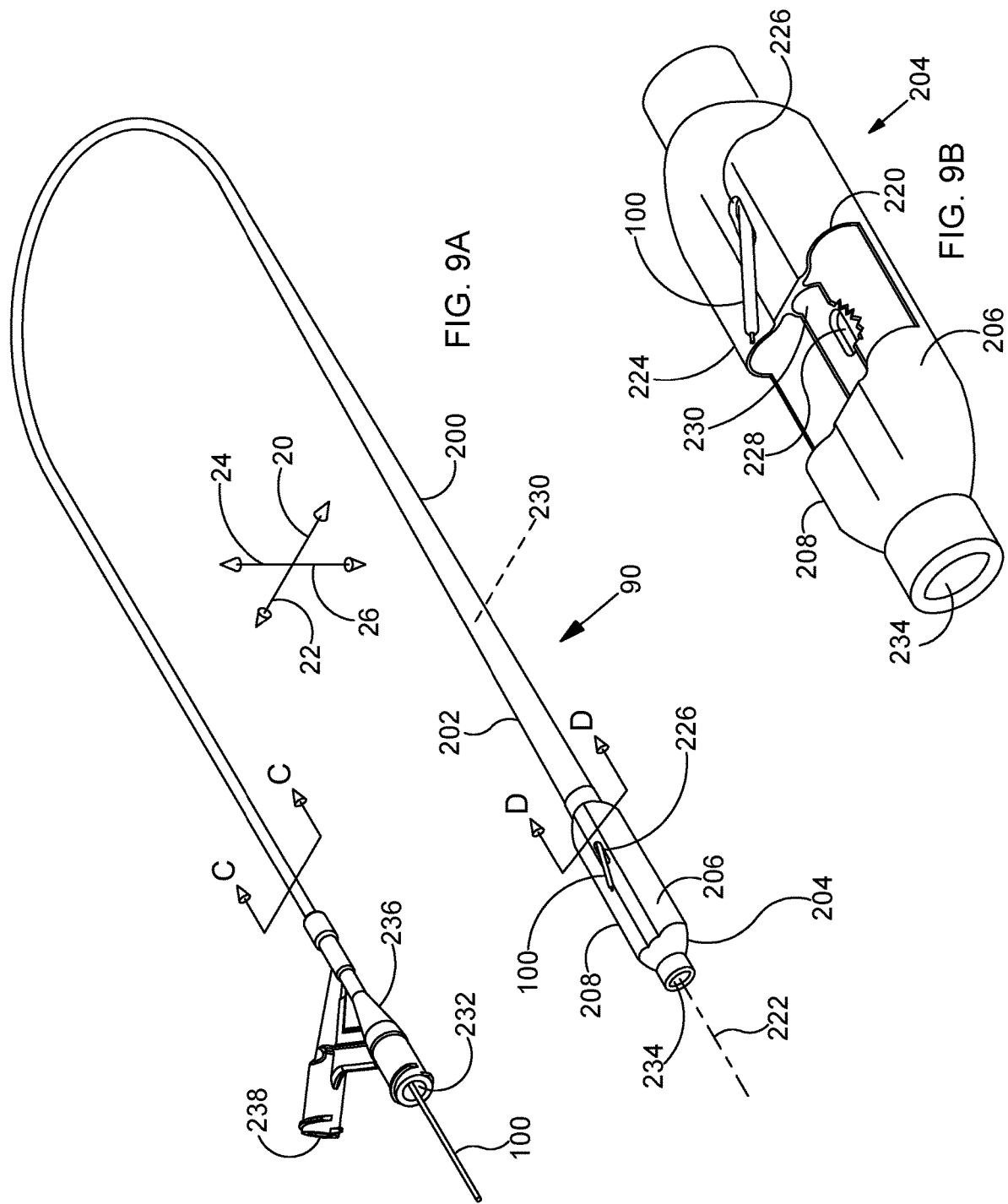

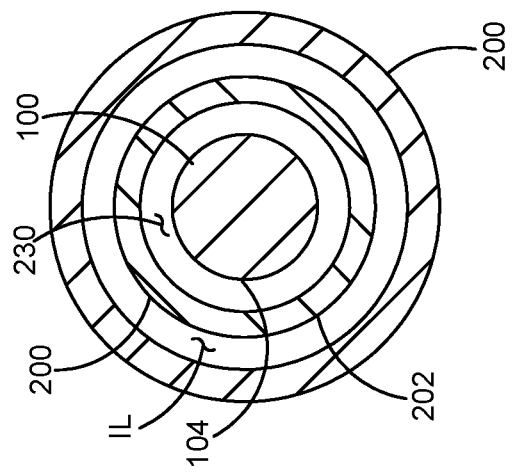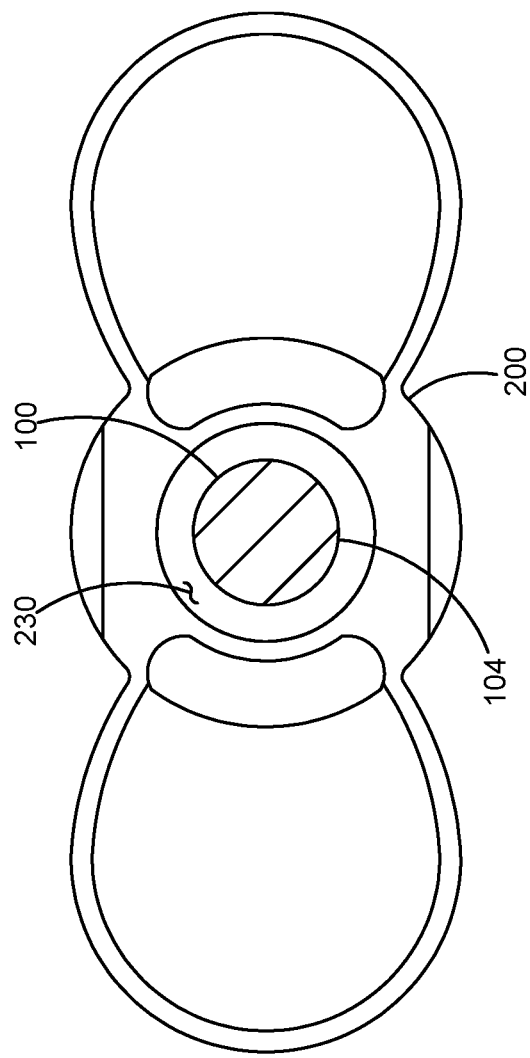

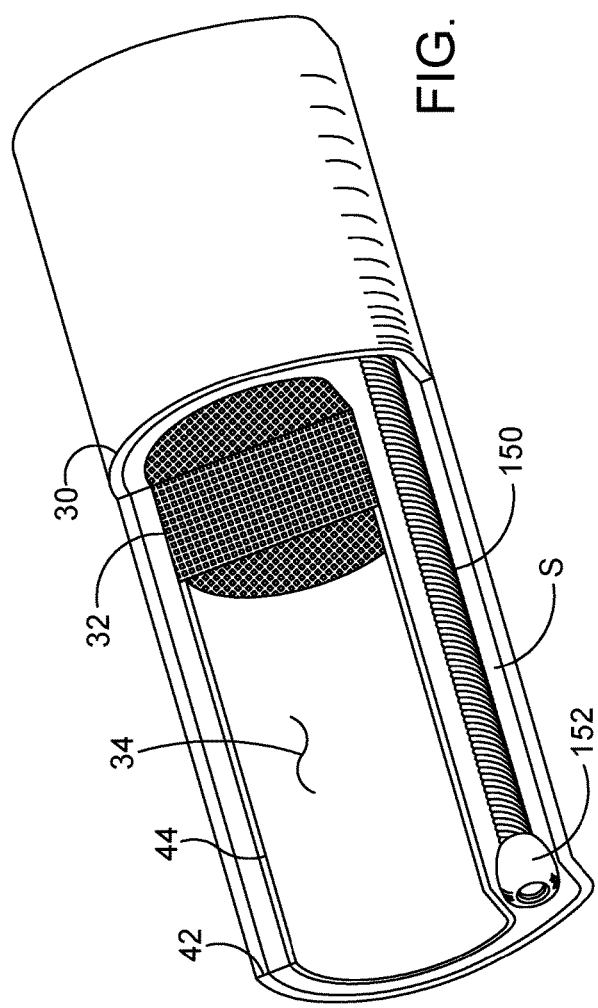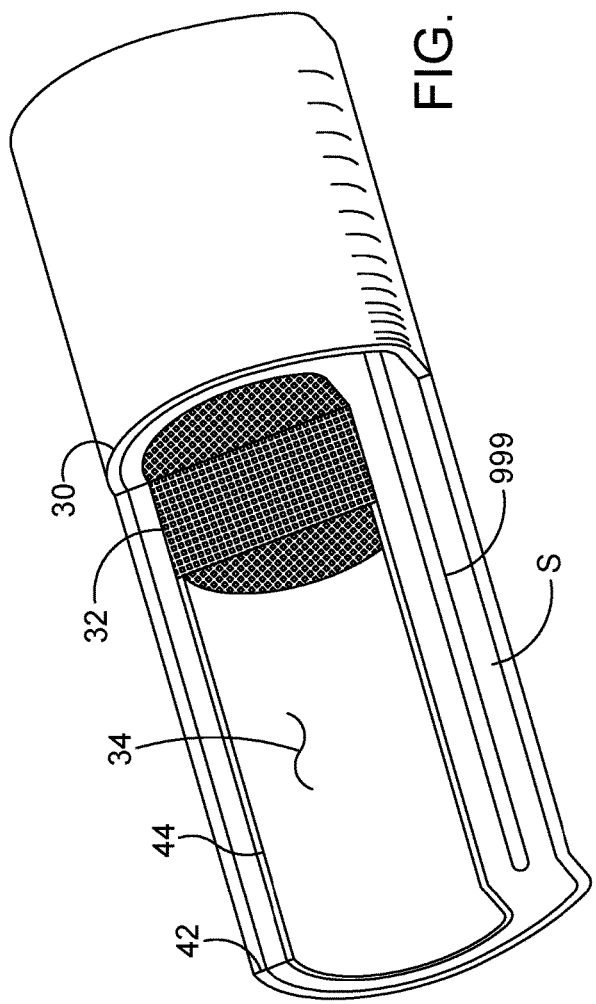

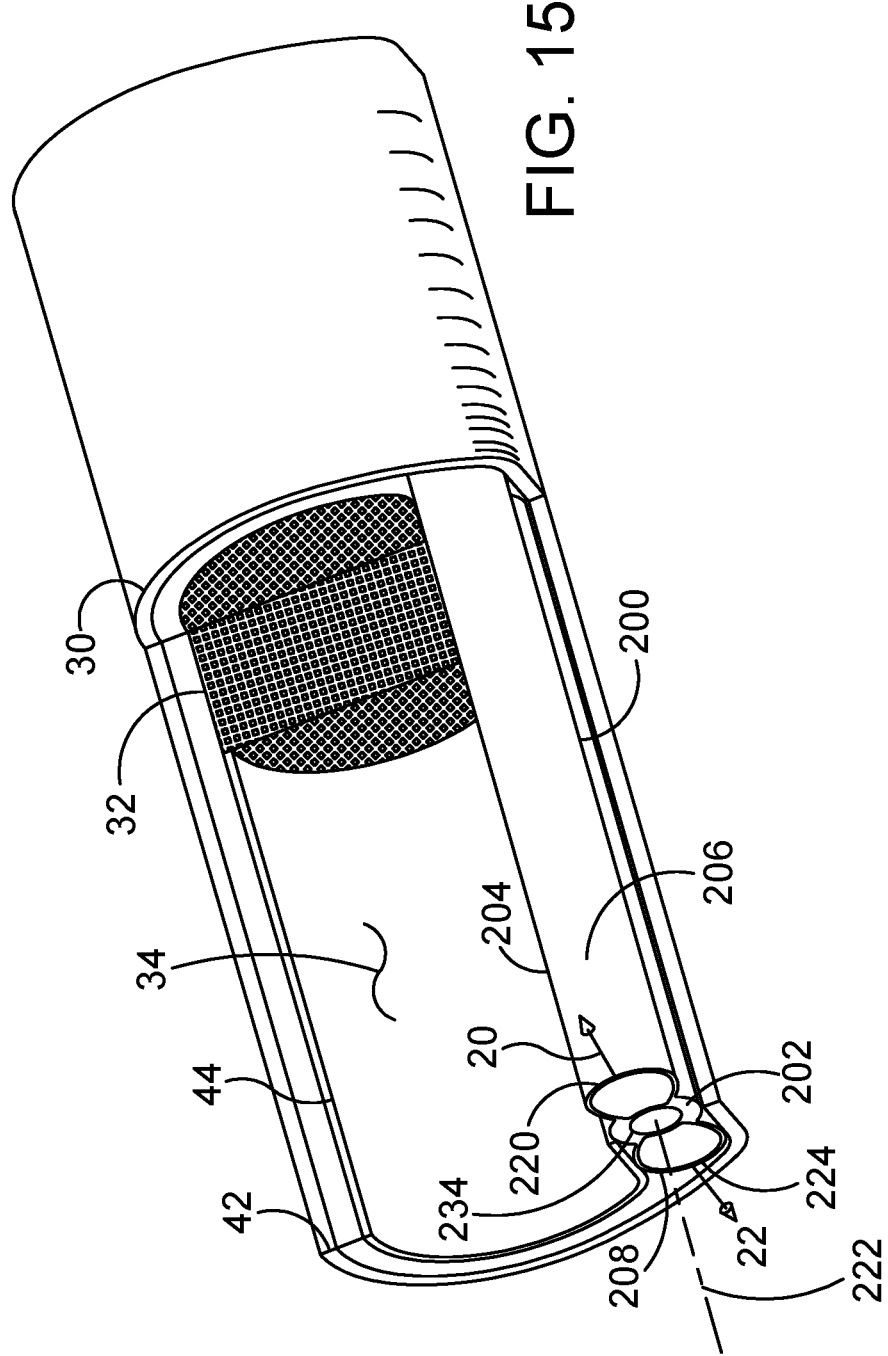

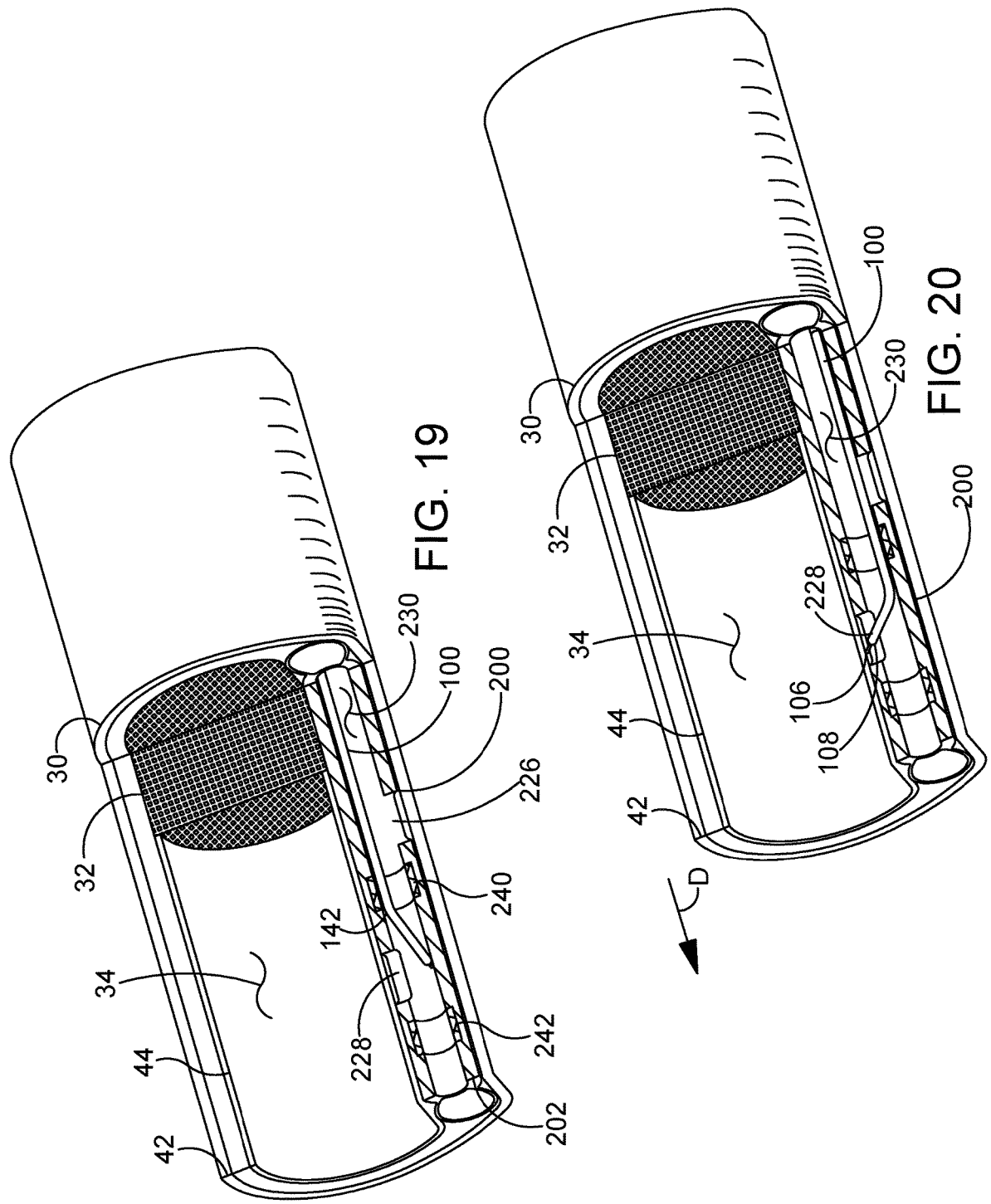

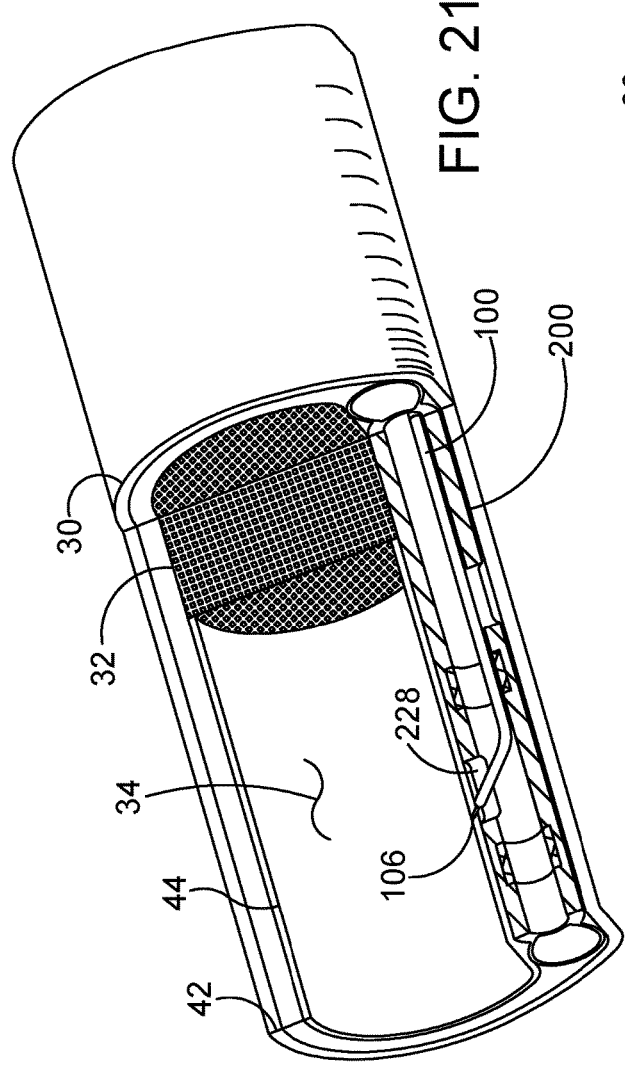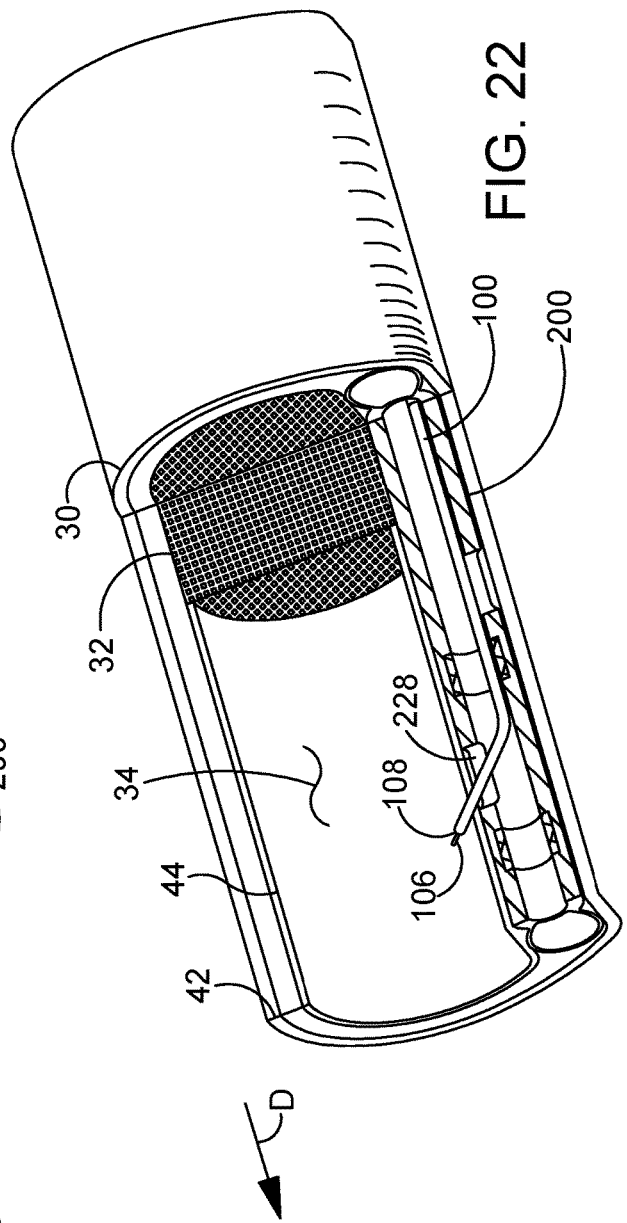

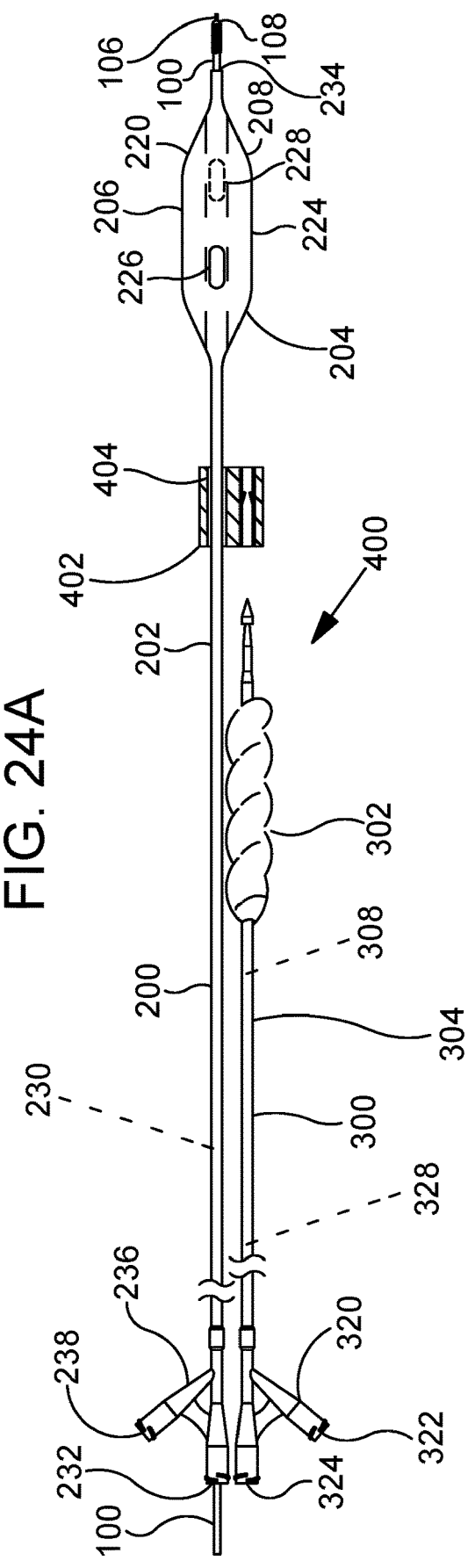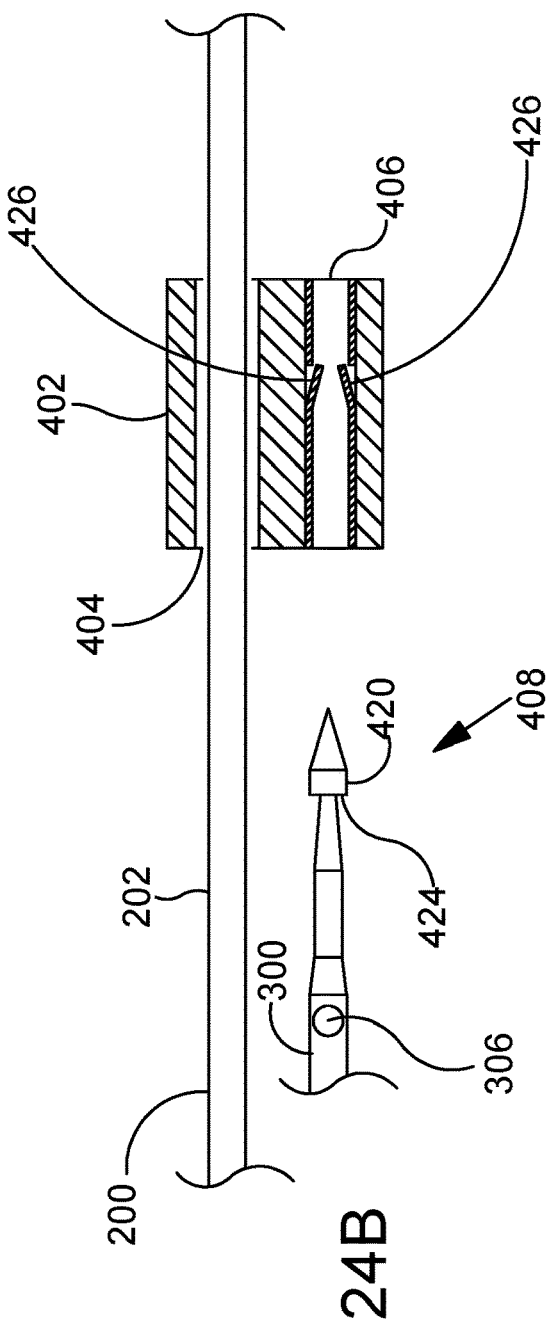
FIG. 24A
FIG. 24B

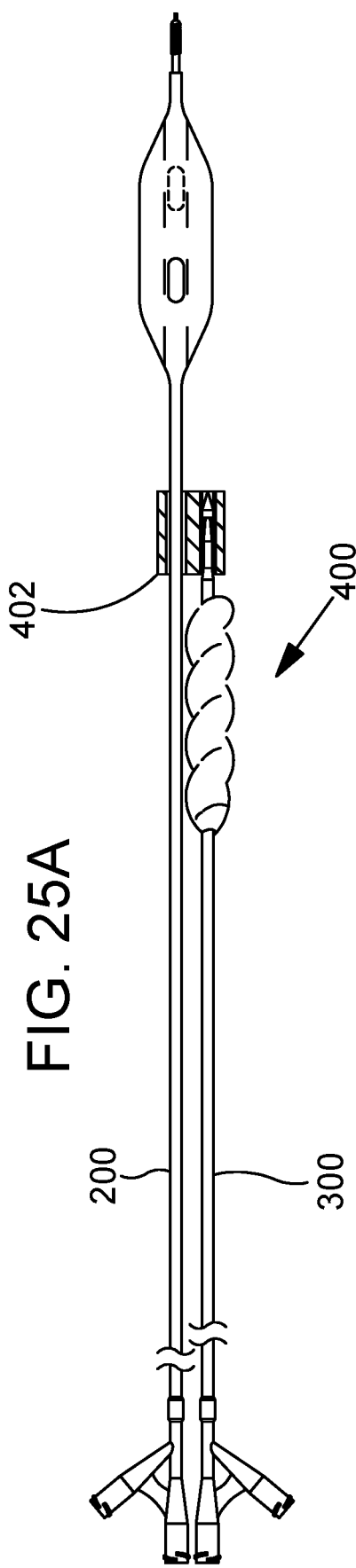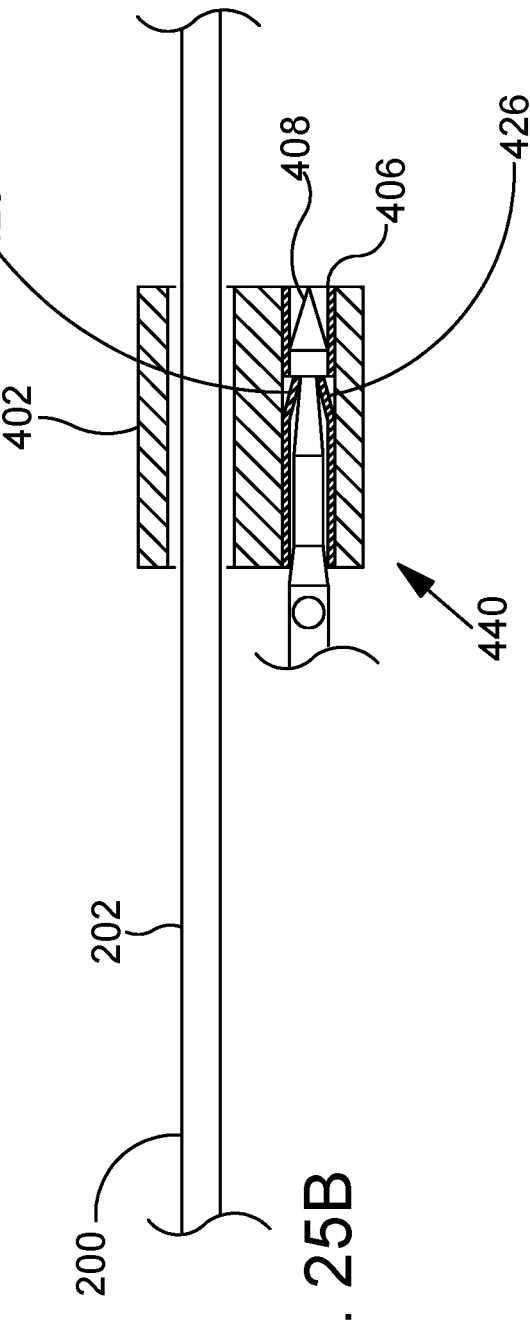
FIG. 25A
FIG. 25B

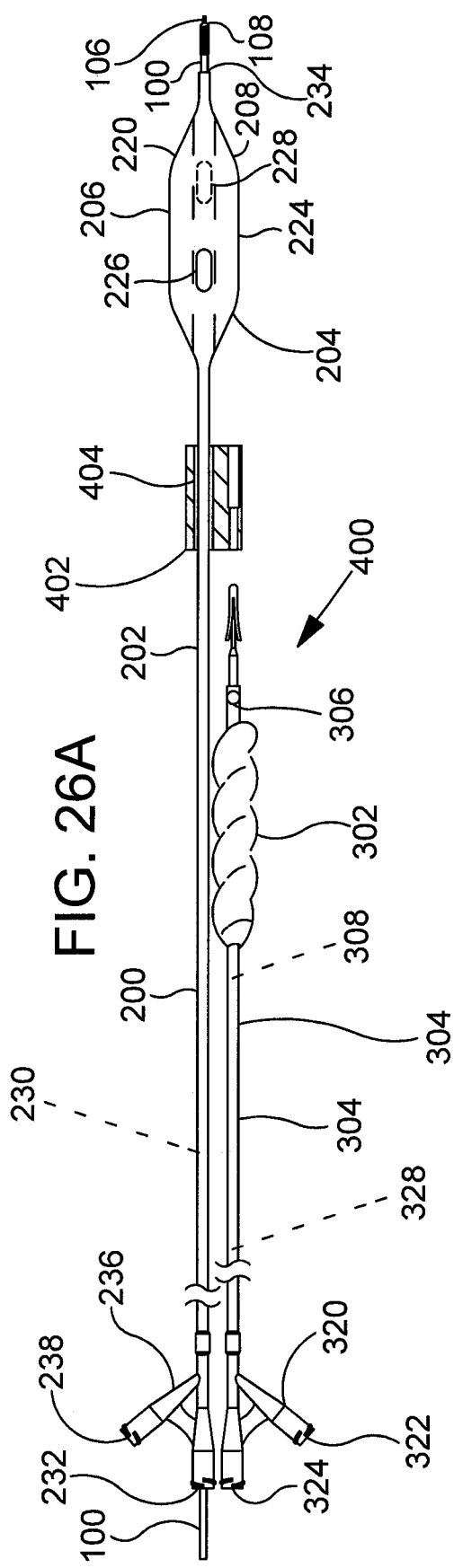
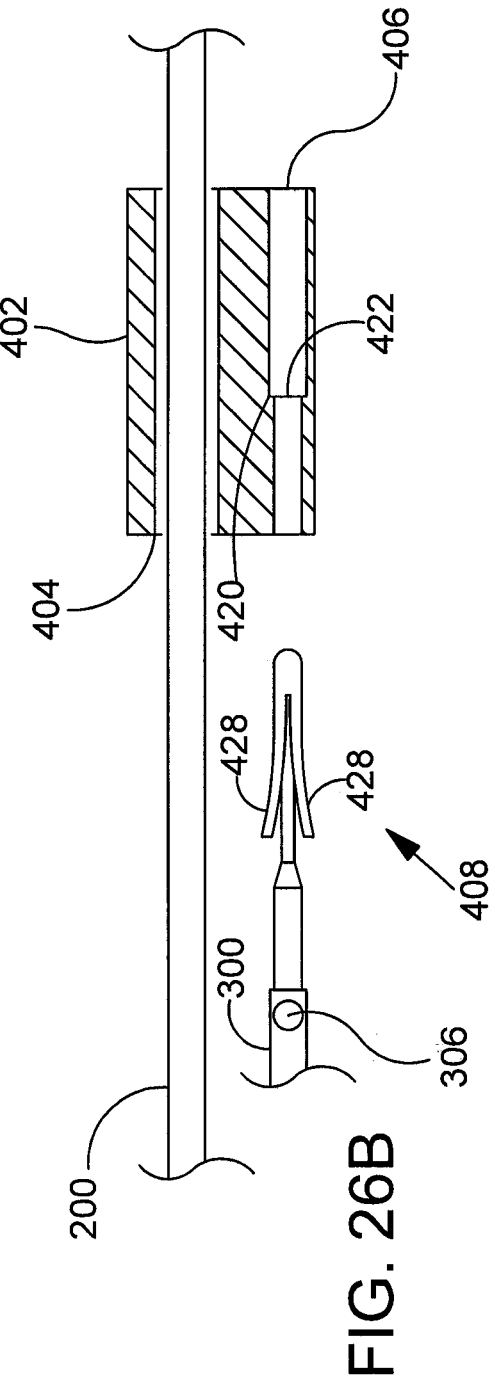
FIG. 26A
FIG. 26B

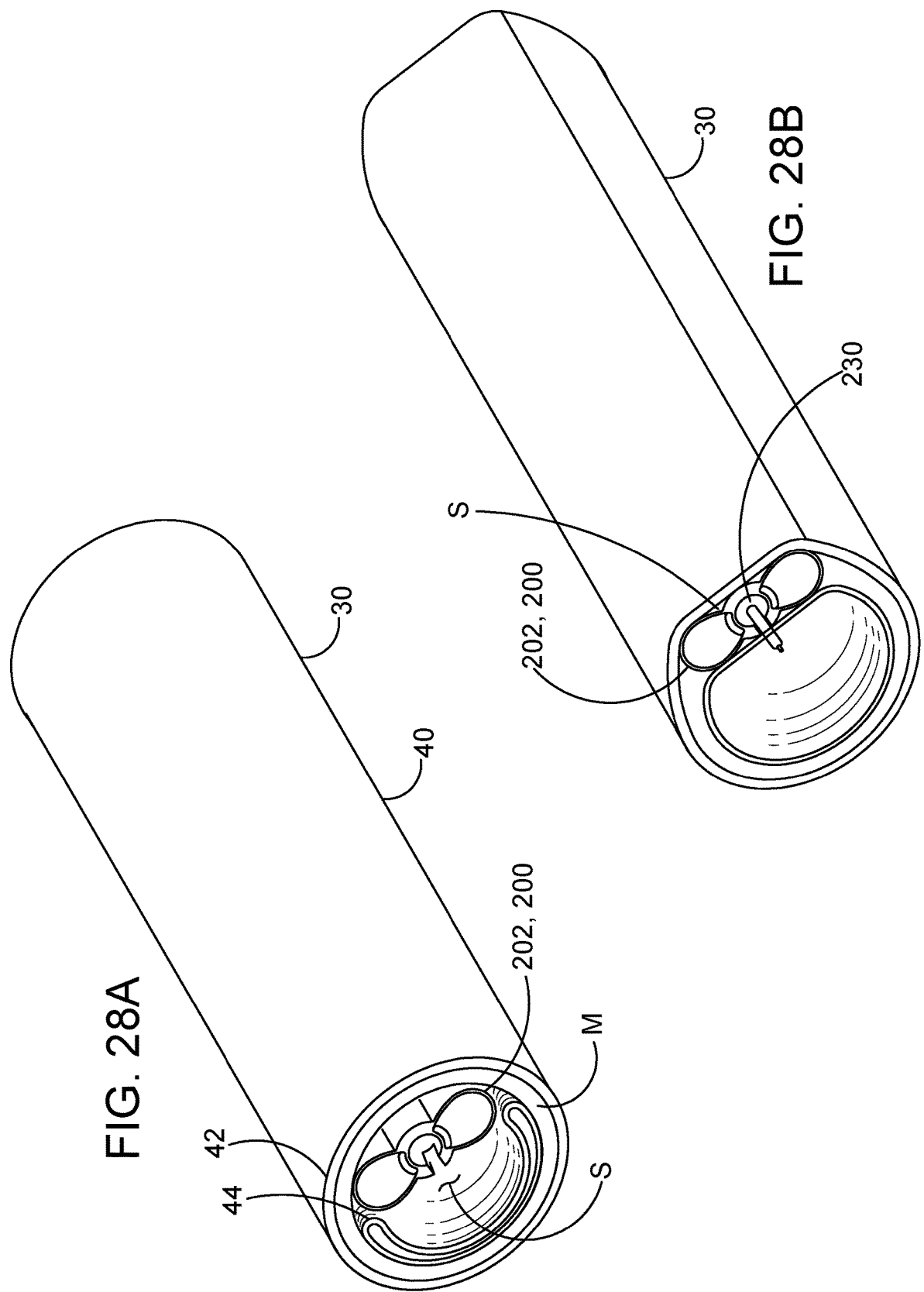

SYSTEMS, APPARATUS AND METHODS FOR TREATING BLOOD VESSELS

CROSS REFERENCE TO RELATED APPLICATION

This application is a continuation of U.S. application Ser. No. 14/205,901, filed Mar. 12, 2014, which claims the benefit of U.S. Provisional Application Ser. No. 61/781,217, filed Mar. 14, 2013, the entire disclosures of which are incorporated herein by reference.

TECHNICAL FIELD

This disclosure relates to systems and devices for treating chronic occlusions in blood vessels and associated methods. More particularly, this disclosure relates to devices for establishing a blood flow path around a chronic total occlusion and methods for fabricating those devices.

BACKGROUND

A number of diseases are caused by the build-up of plaque in the arteries. These plaque deposits limit blood flow to the tissues that are supplied by that particular artery. When these deposits build up in the arteries of the heart, the problem is called coronary artery disease (CAD). When these deposits build up in the arteries of a limb, such as a leg, the condition is called peripheral artery disease (PAD).

Peripheral artery disease affects 8 to 12 million individuals in the United States and is also prevalent in Europe and Asia. Roughly 30% of the population over the age of 70 suffers from PAD. PAD typically causes muscle fatigue or pain brought about by exertion and relieved by rest. Symptoms of PAD can include leg pain during walking and wounds that do not heal. The inability to walk without leg pain often causes patients to stop exercising and reduces the patient's mobility. When the plaque builds up to the point where an artery is totally occluded, the obstruction is referred to as a Chronic Total Occlusion (CTO). A CTO that occludes the peripheral arteries for PAD patients is extremely serious. PAD patients that suffer from a CTO often enter a downward spiral towards death. Often the CTO in a peripheral artery results in limb gangrene, which requires limb amputation to resolve. The limb amputation in turn causes other complications, and roughly half of all PAD patients die within two years of a limb amputation.

The blood pumping action of the heart muscle is critical to sustaining the life of a patient. In order for the heart to function properly the tissues of the heart muscle must be continuously supplied and re-supplied with oxygen. To receive an adequate supply of oxygen, the heart muscle must be well perfused with blood. In a healthy heart, blood perfusion is accomplished with a system of arteries and capillaries. However, due to age, high cholesterol and other contributing factors, a large percentage of the population has arterial atherosclerosis that totally occludes portions of the patient's coronary arteries. A chronic total occlusion (CTO) in a coronary artery may cause painful angina, atrophy of cardiac tissue and patient death.

SUMMARY

The disclosure is directed to several alternative designs, materials and methods of manufacturing medical device structures and assemblies, and uses thereof.

Accordingly, one illustrative embodiment is a system for treating a blood vessel including a blood vessel wall defining a blood vessel lumen where the blood vessel lumen is at least partially obstructed by an occlusion. The occlusion divides the lumen into a proximal lumen segment and a distal lumen segment. The system includes an orienting catheter and an occlusion catheter. The orienting catheter includes an orienting catheter shaft carrying an orienting element and a tracking element advanceable along the orienting catheter shaft. The occlusion catheter includes a balloon and a coupling element configured to engage a complementary coupling element of the tracking element to form a connection therebetween. The occlusion catheter defines an inflation lumen disposed in fluid communication with an interior of the balloon so that the balloon can be selectively inflated by injecting an inflation fluid through the inflation lumen. The balloon, when in an inflated state, is sized so as to occlude the blood vessel lumen to isolate a target volume defined by blood vessel tissues. The occlusion catheter defines an aspiration lumen disposed in fluid communication with a distal port positioned so that fluid can be withdrawn from the target volume and into the aspiration lumen.

Another illustrative embodiment is a method for treating a blood vessel including a blood vessel wall defining a blood vessel lumen, where the blood vessel lumen is at least partially obstructed by an occlusion. The occlusion divides the lumen into a proximal lumen segment and a distal lumen segment. The method includes positioning an orienting element of an orienting catheter inside an intrawall space located distal of the occlusion from the proximal lumen segment. The intrawall space is located between an intima and an adventitia of the blood vessel wall. An occluding element of an occlusion catheter is positioned in the proximal lumen segment at a location near the occlusion. The occluding element includes a balloon. The balloon of the occlusion catheter is inflated in the proximal lumen segment so as to isolate a target volume. The target volume includes the intrawall space. The pressure inside the target volume is reduced. The orienting element is deployed in the intrawall space so that the orienting catheter assumes an orientation in which a port of the orienting catheter is directed toward the distal lumen segment. A distal end of a reentry device is advanced from the port through the intima and into the distal lumen segment.

Yet another illustrative embodiment is a method for treating a blood vessel including a blood vessel wall defining a blood vessel lumen, where the blood vessel lumen is at least partially obstructed by an occlusion. The occlusion divides the lumen into a proximal lumen segment and a distal lumen segment. The method includes positioning an orienting element of an orienting catheter inside an intrawall space located distal of the occlusion from the proximal lumen segment. The intrawall space is located between an intima and an adventitia of the blood vessel wall. An occluding element of an occlusion catheter is positioned in the proximal lumen segment at a location near the occlusion. The occluding element includes a balloon. The balloon of the occlusion catheter is inflated in the proximal lumen segment so as to isolate a target volume. The target volume includes the intrawall space. The volume of the target volume is reduced so that the intima presses against the orienting element of the orienting catheter. The orienting element is deployed in the intrawall space so that the orienting catheter assumes an orientation in which a port of the orienting catheter is directed toward the distal lumen segment. The distal end of a reentry device is advanced from the port through the intima and into the distal lumen segment.

The above summary of some example embodiments is not intended to describe each disclosed embodiment or every implementation of the aspects of the disclosure.

BRIEF DESCRIPTION OF THE DRAWINGS

FIG. 3 is a stylized perspective view illustrating a blood vessel having a wall comprising three layers.

FIG. 4 is an additional stylized perspective view of a blood vessel having a wall including an adventitia, a media, and an intima.

In FIG. 6 an angiographic image illustrating the vasculature of the heart is projected onto the display screen.

FIGS. 7A-7C diagramically illustrate exemplary situations that may disrupt a physician's ability to visualize a portion of a patient's vasculature.

FIG. 8A is a stylized depiction of a heart including a blood vessel.

FIG. 8B is a stylized depiction of a display screen that is part of a fluoroscopy system. In FIG. 8B an angiographic image illustrating the blood vessel shown in FIG. 8A is projected onto the display screen.

FIG. 8C is an additional stylized depiction of the blood vessel and heart shown in FIG. 8A.

FIG. 8D is a stylized depiction of a display screen that is part of a fluoroscopy system. In FIG. 8D an angiographic image illustrating the blood vessel shown in FIG. 8C is projected onto the display screen.

FIG. 9A is a perspective view showing an assembly including an orienting catheter and a re-entry device. The assembly of FIG. 9A may be used, for example, to establish a blood flow path between a proximal segment of a blood vessel and a distal segment of a blood vessel that are separated by an occlusion.

FIG. 9B is an enlarged isometric view further illustrating a portion of the assembly shown in FIG. 9A.

FIG. 9C is a cross-section view taken along section line C-C shown in FIG. 9A.

FIG. 9D is a cross-section view taken along section line D-D shown in FIG. 9A.

FIG. 10 through FIG. 22 are a series of stylized fragment views illustrating various steps that may be included as part of the methods in accordance with the detailed description. The apparatus described herein may be useful, for example, when performing these methods.

FIG. 24A is a plan view showing a system in accordance with the detailed description.

FIG. 24B is an enlarged plan view further illustrating a portion of the system shown in FIG. 24A.

FIG. 25A is an additional plan view illustrating a second configuration of the system shown in FIGS. 24A-24B.

FIG. 25B is an enlarged plan view further illustrating a portion of the system shown in FIG. 25A.

FIG. 26A is a plan view showing a system in accordance with the detailed description.

FIG. 26B is an enlarged plan view further illustrating a portion of the system shown in FIG. 26A.

FIG. 28A is a stylized pictorial view of a blood vessel having a wall including an adventitia, a media, and an intima.

FIG. 28B is an additional stylized pictorial view of the blood vessel shown in FIG. 28A.

DETAILED DESCRIPTION

The following detailed description should be read with reference to the drawings in which similar elements in different drawings are numbered the same. The drawings, which are not necessarily to scale, depict illustrative embodiments and are not intended to limit the scope of the disclosure.

Figure 1:
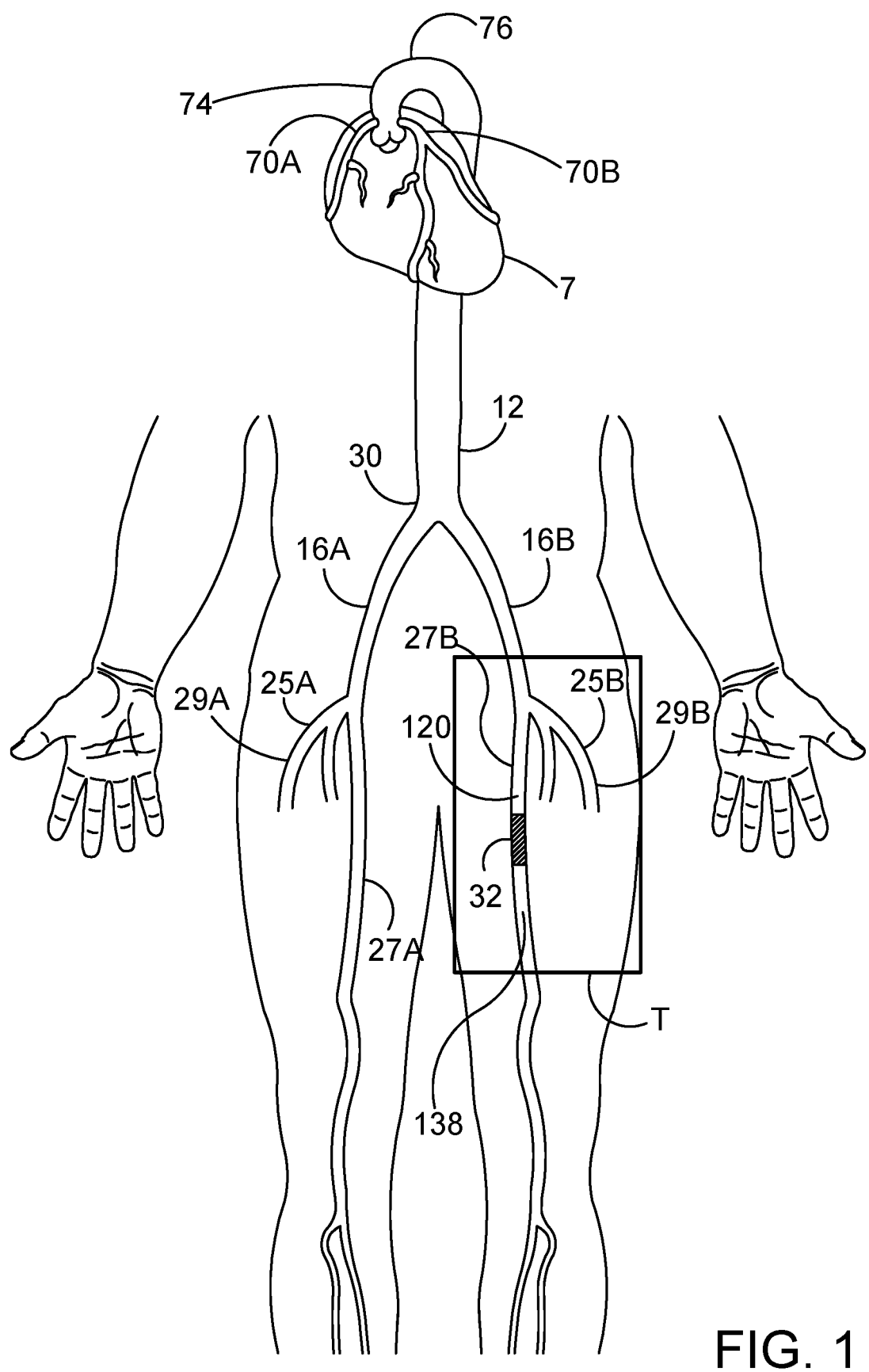
FIG. 1 is a stylized anterior view showing a human patient. A portion of the patient's arterial system is schematically illustrated in FIG. 1.

FIG. 1 is a stylized anterior view illustrating the cardiovascular system of a human patient. The cardiovascular system of FIG. 1 includes a heart 7 that pumps blood and an arterial system that distributes oxygen rich blood throughout the body. During each heartbeat, the left ventricle of heart 7 contracts, pumping blood through the aortic valve and into the ascending aorta 74. Blood from the ascending aorta 74 flows through the aortic arch 76 and down the descending aorta 12 to the lower body. Blood from the ascending aorta 74 also flows into the left coronary artery 70B and the right coronary artery 70A. In a healthy heart, the left coronary artery 70B and the right coronary artery 70A provide a continuous flow of blood to the heart which assures that the heart muscle remains well oxygenated.

The descending aorta 12 gives off numerous branches that supply oxygenated blood to the chest cage and the organs within the chest. The descending aorta 12 continues to the iliac bifurcation 30, which is a branch that splits into the two common iliac arteries 16A and 16B. The iliac arterial vasculature includes two branches continuing from the iliac bifurcation 30. The right branch includes the right common iliac artery 16A, which bifurcates into the right external iliac artery 25A and the right internal iliac artery 27A. When the right external iliac artery 25A passes posterior to the inguinal ligament, it becomes the right femoral artery 29A of the right leg. The left branch of the iliac arterial vasculature includes the left common iliac artery 16B, which bifurcates into the left external iliac artery 25B and the left internal iliac artery 27B. When the left external iliac artery 25B passes posterior to the inguinal ligament, it becomes the left femoral artery 29B of the left leg.

In the exemplary embodiment of FIG. 1, an occlusion 32 is blocking blood flow through a portion of a blood vessel within a target region T of the patient's arterial system. The occlusion 32 is obstructing blood flow between a proximal segment 120 of the blood vessel and a distal segment 138 of the blood vessel. A system in accordance with the present detailed description may be used to establish a blood flow path between proximal segment 120 and distal segment 138.

Figure 2A:
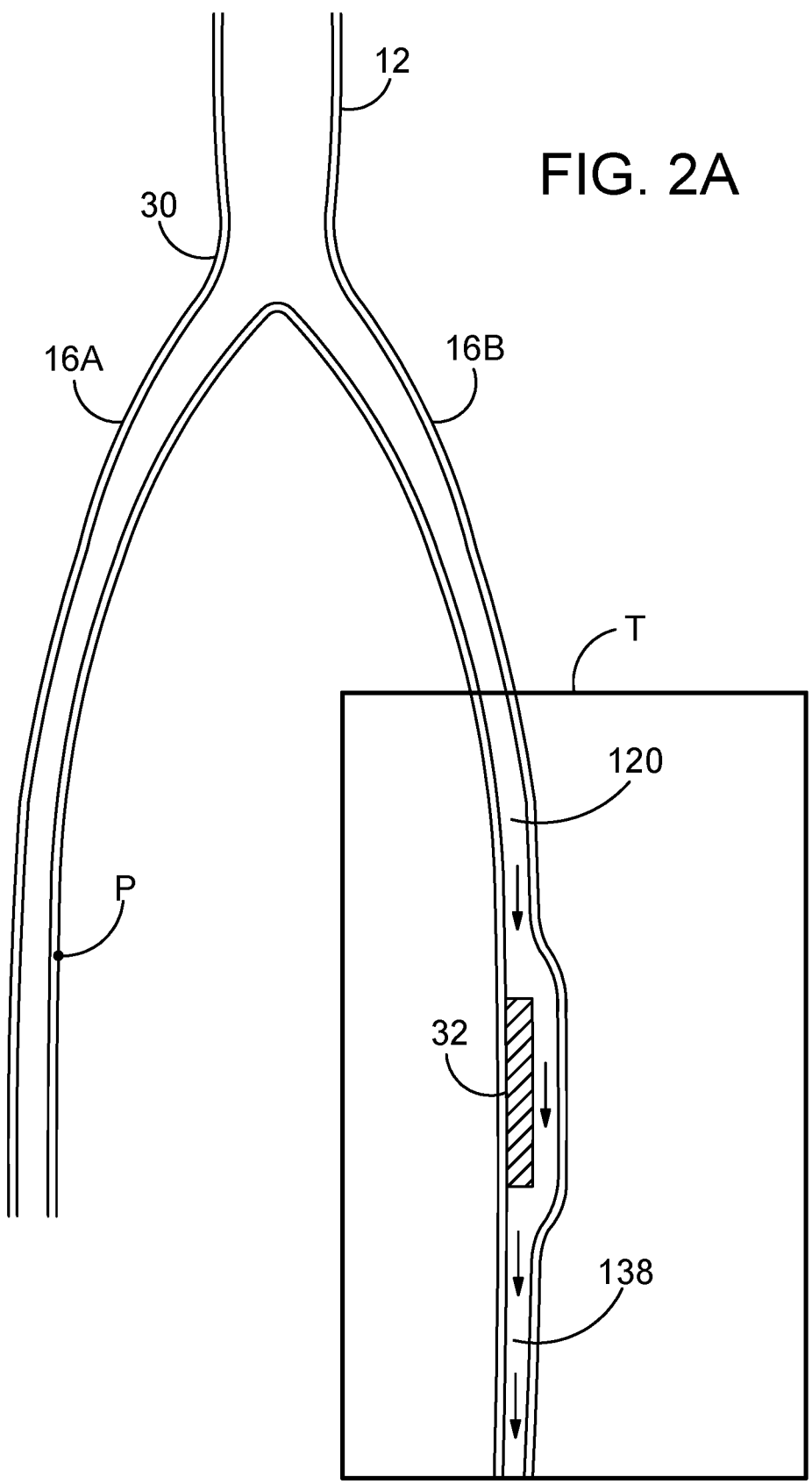
FIG. 2A is an enlarged schematic view showing a portion of the arterial system of a patient who has been treated for peripheral artery disease (PAD).

FIG. 2A is an enlarged schematic view showing a portion of the arterial system of a patient who has been treated for peripheral artery disease (PAD). The portion of the arterial system shown in FIG. 2A includes the descending aorta 12, the iliac bifurcation 30, the right common iliac artery 16A and the left common iliac artery 16B. In the exemplary embodiment of FIG. 2A, the patient's condition has been treated by establishing a blood flow path around an occlusion 32. The blood flow around occlusion 32 is illustrated using arrows in FIG. 2A. The portion of the arterial system located in target region T may be treated using a contralateral approach. When using the contralateral approach, an endovascular device may enter the vascular system at an access point P. After entering the arterial system the endovascular device may be advanced through iliac bifurcation 30 to reach the target region T in the leg opposite the leg that is the site of access. In other instances, another approach may be used to reach the target region T.

Figure 2B:
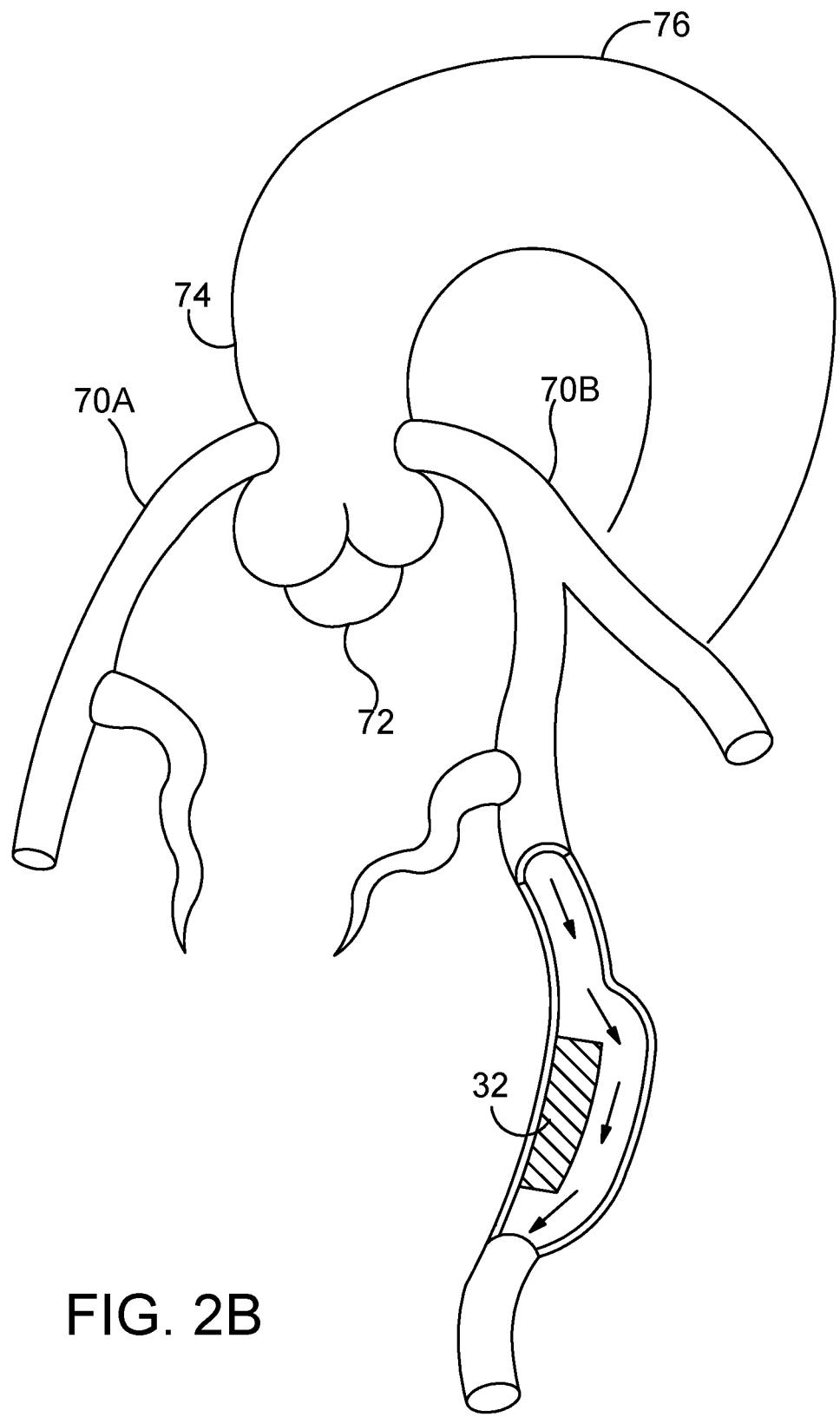
FIG. 2B is an enlarged schematic view showing a portion of the arterial system of a patient who has been treated for coronary artery disease (CAD).

FIG. 2B is an enlarged schematic view showing a portion of the arterial system of a patient who has been treated for coronary artery disease (CAD). The portion of the arterial system shown in FIG. 2B includes the aortic valve 72, the right coronary artery 70A, the left coronary artery 70B, the ascending aorta 74, and the aortic arch 76. Left coronary artery 70B and right coronary artery 70A each meet the ascending aorta 74 at an ostium. During the systolic phase of each cardiac cycle, oxygen rich blood from the ascending aorta 74 flows through left coronary artery 70B and right coronary artery 70A. In a healthy heart, this oxygen rich blood is distributed throughout the heart by a network of arteries and capillaries.

In the exemplary embodiment of FIG. 2B, the patient's condition has been treated by establishing a blood flow path around an occlusion 32. The blood flow around occlusion 32 is illustrated using arrows in FIG. 2B. In the exemplary embodiment of FIG. 2B, occlusion 32 is located in left coronary artery 70B. The methodology for treating a coronary artery may include inserting a guide catheter into a femoral artery and advancing the guide catheter such that its distal tip moves through that artery, up the descending aorta, through the aortic arch and ultimately into the ostium of the coronary artery. A system in accordance with this detailed description may then be advanced through the guide catheter into the coronary artery. Once in the coronary artery, the system may be used to establish a blood flow path between a proximal segment of the coronary artery and a distal segment of the coronary artery. In other instances, another approach may be used to treat the coronary artery.

FIG. 3 is a stylized perspective view illustrating a blood vessel 30 having a wall 40. In FIG. 3, wall 40 of blood vessel 30 is shown having three layers. The outermost layer of wall 40 is the adventitia 42 and the innermost layer of wall 40 is the intima 44. Intima 44 defines a true lumen 34 of blood vessel 30. The tissues extending between intima 44 and adventitia 42 may be collectively referred to as the media M. For purposes of illustration, intima 44, media M and adventitia 42 are each shown as a single homogenous layer in FIG. 3. In the human body, however, the intima 44 and the media M each comprise a number of sub-layers. The transition between the external most portion of the intima 44 and the internal most portion of the media M is sometimes referred to as the subintimal space. In the embodiment of FIG. 3, an occlusion 32 is blocking the true lumen 34 of blood vessel 30. Occlusion 32 divides true lumen 34 into a proximal lumen segment 36 and a distal lumen segment 38.

FIG. 4 is an additional stylized perspective view of a blood vessel 30 having a wall 40 including an adventitia 42, a media M, and an intima 44. In the embodiment of FIG. 4, a portion of intima 44 has become separated from the other layers of blood vessel wall 40. This situation may occur, for example, when a physician has passed one or more prolapsed guidewires, or other medical device, between intima 44 and adventitia 42. A prolapsed guidewire is a guidewire having a distal tip that has been bent to form a loop or knuckle. The human heart includes a number of blood vessels having the general structure illustrated in FIG. 4. Examples of these blood vessels include the left coronary artery and the right coronary artery.

Figure 5:
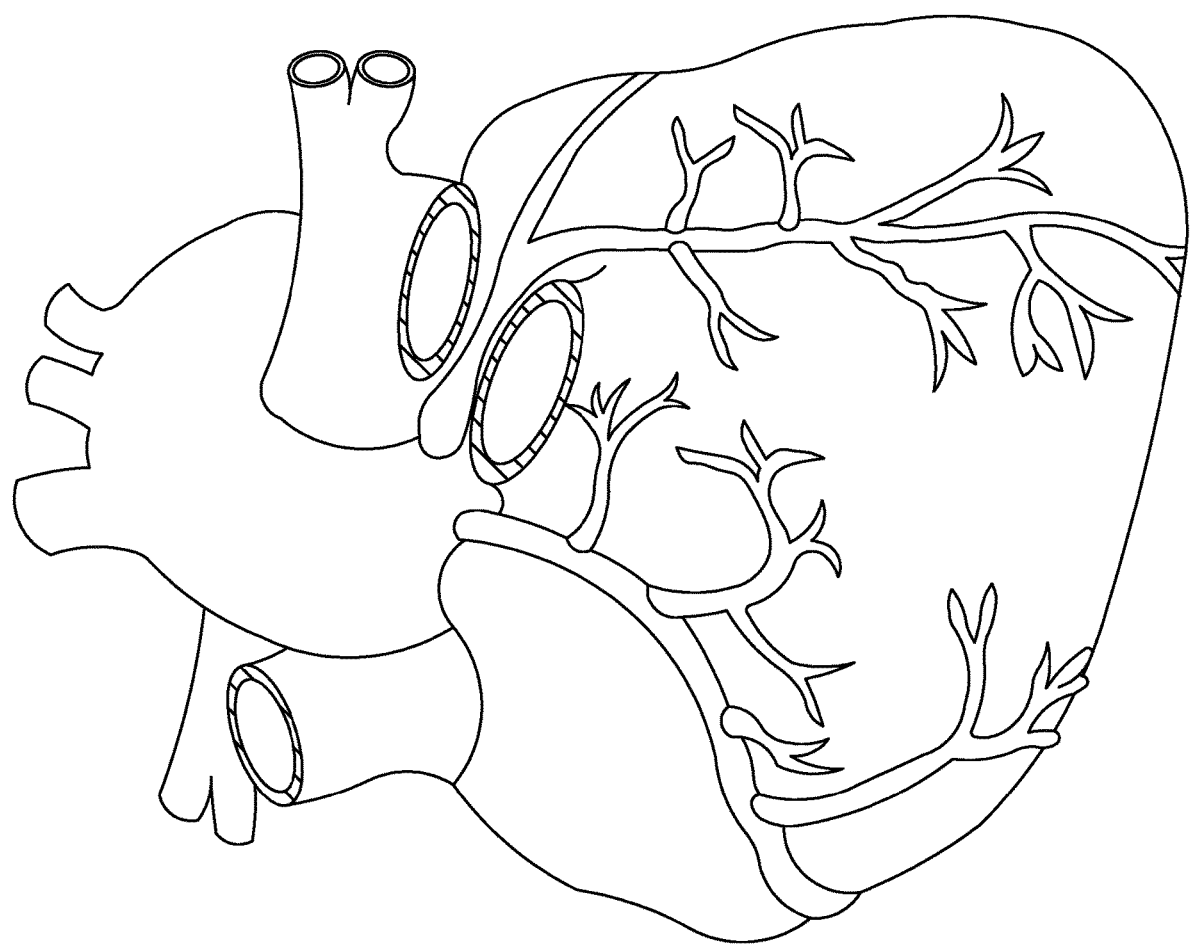
FIG. 5 is a stylized drawing showing a human heart.

FIG. 5 is a stylized drawing showing a human heart. The heart of FIG. 5 includes a plurality of coronary arteries, all of which are susceptible to occlusion. Under certain physiological circumstances and given sufficient time, some occlusions may become total or complete. As used herein, the terms total occlusion and complete occlusion are intended to refer to the same or similar degree of occlusion with some possible variation in the age of the occlusion. Generally, a total occlusion refers to a vascular lumen that is ninety percent or more functionally occluded in cross-sectional to area, rendering it with little to no blood flow therethrough and making it difficult or impossible to pass a conventional guide wire therethrough. Also generally, the older the total occlusion the more organized the occlusive material will be and the more fibrous and calcified it will become. According to one accepted clinical definition, a total occlusion is considered chronic if more than two weeks have passed since the onset of symptoms.

Methods and apparatus disclosed in this detailed description may be useful, for example, to establish a blood flow path around an occlusion (e.g., a total occlusion) in a blood vessel. Methods and apparatus disclosed in this detailed description may also be used to facilitate visualization of a patient's vasculature using fluoroscopic techniques. Fluoroscopy is a medical imaging technique used by physicians to obtain real-time moving images of the internal structures of a patient through the use of a fluoroscope. During a procedure utilizing fluoroscopy, a radio-opaque contrast agent is injected into the blood stream in a selected area of the patient's vasculature. This causes blood flowing through the selected areas to become visible on a display screen.

Figure 6:
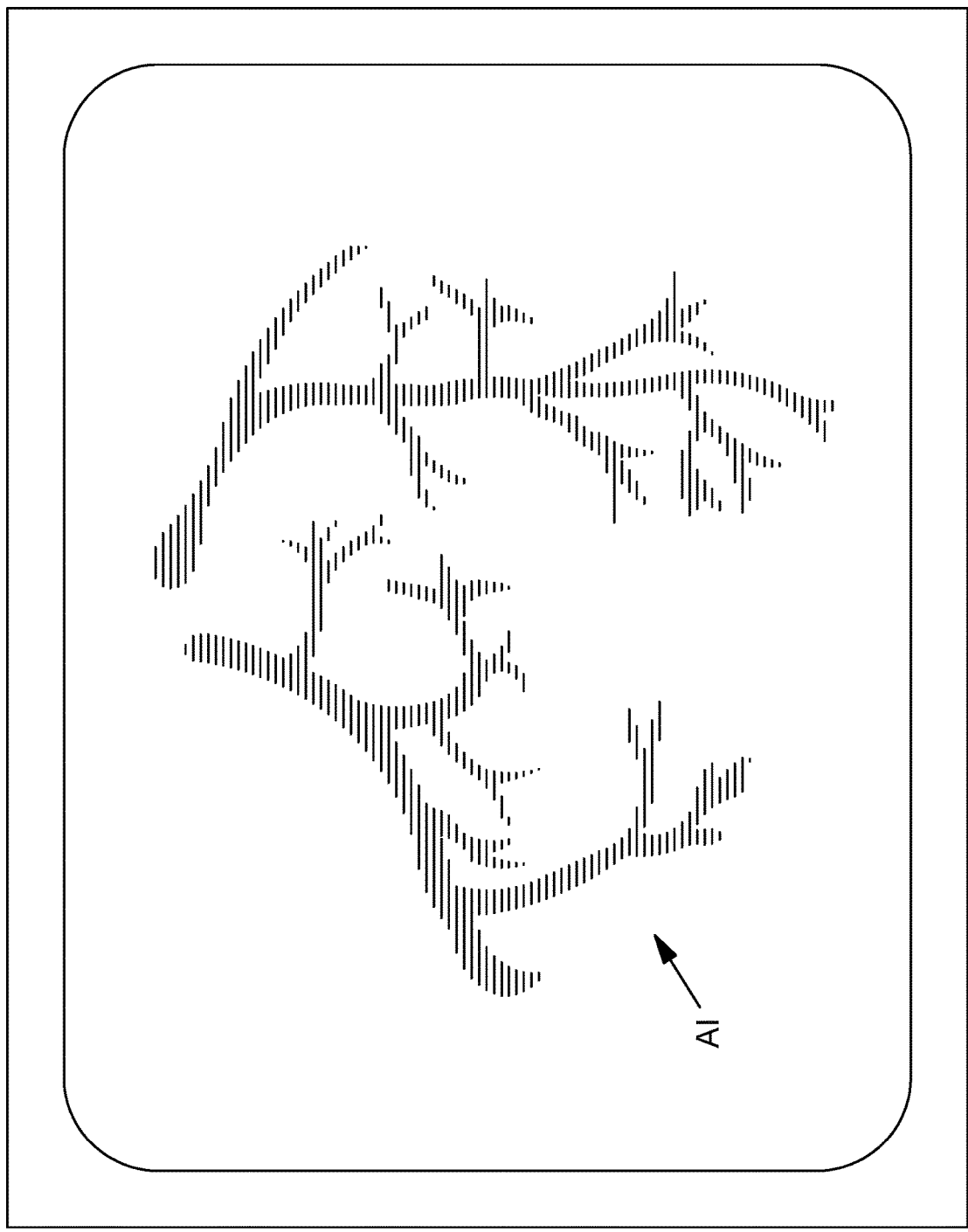
FIG. 6 is a stylized depiction of a display screen that is part of a fluoroscopy system.

FIG. 6 is a stylized depiction of a display screen FD that is part of a fluoroscopy system. In FIG. 6 an angiographic image AI illustrating the vasculature of the heart is projected onto display screen FD. Fluoroscopic systems that may be suitable in some applications are commercially available from GE Heathcare (Chalfont, St. Giles, UK) and Siemens (Munchen, Bayern, DE).

A physician's ability to visualize a portion of a patient's vasculature may be disrupted during some medical procedures. In some cases, this disruption may make it difficult or impossible for the physician to successfully complete the procedure. FIGS. 7A-7C are somewhat symbolic diagrams illustrating exemplary situations that may disrupt a physician's ability to visualize a portion of a patient's vasculature.

FIG. 7A is a stylized diagram showing a portion of a blood vessel 30 that is being treated by a physician. In FIG. 7A, an occlusion 32 can be seen dividing true lumen 34 of blood vessel 30 into a proximal lumen segment 36 and a distal lumen segment 38. Proximal lumen segment 36 is generally in fluid communication with the left ventricle of the heart.

Distal lumen segment 38 is generally in fluid communication with the right atrium of the heart. As the left ventricle pumps blood into proximal segment 36, the fluid in that area of the blood vessel 30 will have a ventral pressure PV. At the same time, the blood in distal segment 38 will have an atrial pressure PA. Due to the blood pumping action of the heart, ventral pressure PV is generally greater than atrial pressure PA. Accordingly, it will be appreciated that there is a pressure differential across occlusion 32 in the embodiment of FIG. 7A.

In the embodiment of FIG. 7B, a physician has created an intrawall space S extending between intima 44 and adventitia 42 of blood vessel wall 40. Intrawall space S may be created, for example, by moving one or more prolapsed guidewires, or other medical device, between intima 44 and adventitia 42. A prolapsed guidewire may also be moved between occlusion 32 and adventitia 42, thereby establishing fluid communication between proximal lumen segment 36 and intrawall space S. In the embodiment of FIG. 7B, blood from proximal lumen segment 36 has filled intrawall space S.

In the embodiment of FIG. 7B, the blood inside intrawall space S is generally at ventricle pressure PV and the blood inside distal lumen segment 38 is generally at atrial pressure PA. Accordingly, there is a pressure differential across intima 44 in the embodiment of FIG. 7B. This pressure differential has caused intrawall space S to fill with blood from proximal lumen segment 36 in the embodiment of FIG. 7B.

FIG. 7C is an additional stylized representation of blood vessel 30 and intrawall space S. By comparing FIG. 7C with FIG. 7B, it will be appreciated that the length L of intrawall space S has become greater. In the exemplary embodiment of FIG. 7C, the pressure differential across intima 44 has caused additional dissection of the blood vessel wall. In some cases, the length of a dissection can grow in this way even when that is not the result desired or intended by the physician. As further illustrated in FIG. 8, an elongated dissection can interfere with the physician's ability to "see" a portion of the vasculature using fluoroscopic techniques.

FIG. 8A is a stylized depiction of a heart H including a blood vessel 30. In the embodiment of FIG. 8A, an occlusion 32 is blocking the true lumen 34 of blood vessel 30. Occlusion 32 divides true lumen 34 into a proximal lumen segment 36 and a distal lumen segment 38. During a surgical procedure, a physician may wish to view proximal lumen segment 36 and distal lumen segment 38 of blood vessel 30 using fluoroscopic techniques.

When using fluoroscopic techniques, the physician may inject a radio-opaque contrast agent into the blood stream in the areas near occlusion 32. The radio-opaque contrast agent may be injected into the lumen of blood vessel 30 from both an antegrade direction A and a retrograde direction R. Antegrade direction A and a retrograde direction R are both represented with arrows in FIG. 8A.

FIG. 8B is a stylized depiction of a display screen FD that is part of a fluoroscopy system. In FIG. 8B an angiographic image AI illustrating blood vessel 30 of FIG. 8A is projected onto display screen FD. The radio-opaque contrast agent inside blood vessel 30 has made proximal lumen segment 36 and distal lumen segment 38 visible on display screen FD.

FIG. 8C is an additional stylized depiction of blood vessel 30 and heart H shown in FIG. 8A. In the embodiment of FIG. 8C, a physician has created an intrawall space S extending between intima 44 and adventitia 42 of blood vessel 30. Intrawall space S may be created, for example, by moving one or more prolapsed guidewires, or other medical device, between intima 44 and adventitia 42. A prolapsed guidewire may also be moved between occlusion 32 and adventitia 42, thereby establishing fluid communication between proximal lumen segment 36 and intrawall space S. In the embodiment of FIG. 8C, blood from proximal lumen segment 36 has filled intrawall space S. Also in the embodiment of FIG. 8C, there is a pressure differential across intima 44 between intrawall space S and distal segment 38. This pressure differential is due to the fact that the blood inside the true lumen distal of occlusion 32 is generally at atrial pressure PA and the blood inside intrawall space S is at ventral pressure PV.

Any radio-opaque contrast agent traveling in the retrograde direction R inside true lumen 34 of blood vessel 30 is unlikely to reach the area of distal lumen segment 38 nearest to occlusion 32 because this area of the true lumen 34 is occupied by intrawall space S. Additionally, any radio-opaque contrast agent travelling in the antegrade direction A inside true lumen 34 of blood vessel 30 is unlikely to enter intrawall space S because no blood is leaving intrawall space S to make room for the entering fluid. If no radio-opaque contrast agent enters intrawall space S, then that area of the vasculature cannot be displayed using fluoroscopic techniques.

FIG. 8D is a stylized depiction of a fluoroscopic display screen FD. In FIG. 8D an angiographic image AI illustrating blood vessel 30 of FIG. 8C is projected onto display screen FD. By comparing FIG. 8D with FIG. 8B, it will be appreciated that a substantial portion of distal lumen segment 38 is not visible in angiographic image AI. The portion of blood vessel 30 that is not displayed in angiographic image AI generally corresponds to the portion of distal lumen segment 38 that is occupied by intrawall space S.

FIG. 9A is a perspective view showing an assembly 90 including orienting catheter 200 and re-entry device 100. Assembly 90 may be used, for example, to establish a blood flow path between a proximal segment of a blood vessel and a distal segment of a blood vessel that are separated by a chronic total occlusion. FIG. 9B is an enlarged isometric view further illustrating a portion of assembly 90.

Orienting catheter 200 of FIG. 9A comprises a shaft assembly 202 and an orienting element 204, such as an orienting balloon, that is carried by shaft assembly 202. Orienting element 204 is capable of assuming both a collapsed shape and an expanded shape. Orienting element 204 may be selectively placed in the collapsed shape, for example, while the orienting element 204 is being advanced past an occlusion. Orienting element 204 may be selectively placed in the expanded shape, for example, while the orienting catheter 200 is being used to direct re-entry device 100 toward the lumen of a blood vessel. Orienting element 204 is shown assuming the expanded shape.

Orienting element 204 of orienting catheter 200 comprises a first portion 206 and a second portion 208. In the embodiment of FIG. 9B, first portion 206 of orienting element 204 comprises a first inflatable member 220. Second portion 208 of orienting element 204 comprises a second inflatable member 224 in the embodiment of FIG. 9B.

First inflatable member 220 of orienting element 204 extends in a first direction 20 away from longitudinal axis 222 of shaft assembly 202. Second inflatable member 224 of orienting element 204 extends away from longitudinal axis 222 of shaft assembly 202 in a second direction 22. First direction 20 and second direction 22 are represented with arrows in FIG. 9A. With reference to FIG. 9A, it will be appreciated that second direction 22 is generally opposite first direction 20. In FIG. 9A, the arrows representing first direction 20 and second direction 22 are directed about 180 degrees away from one another.

Shaft assembly 202 of FIG. 9A defines a first aperture 226 and a second aperture 228 (shown in FIG. 9B). In the embodiment of FIG. 9A, first aperture 226 extends away from central lumen 230 in a third direction 24. Second aperture 228 extends away from central lumen 230 in a fourth direction 26. Third direction 24 and fourth direction 26 are represented with arrows in FIG. 9A. In the embodiment of FIG. 9A, third direction 24 and fourth direction 26 extend in generally opposite directions. In FIG. 9A, the arrows representing third direction 24 and fourth direction 26 are directed about 180 degrees away from each other and perpendicular to the first and second directions 20, 22.

A hub 236 is fixed to the proximal end of shaft assembly 202. Hub 236 includes an inflation port 238. Inflation port 238 fluidly communicates with an interior of first inflatable member 220 and second inflatable member 224 via inflation lumens IL defined by shaft assembly 202. The inflatable members 220, 224 may be inflated by injecting an inflation media into inflation port 238. Examples of inflation media that may be suitable in some applications include saline, carbon dioxide, and nitrogen.

Orienting catheter 200 defines a proximal port 232, a distal port 234 and a central lumen 230 that extends between proximal port 232 and distal port 234. In the embodiment of FIG. 9A, proximal port 232 is defined by hub 236 and distal port 234 is defined by shaft assembly 202. Re-entry device 100 may be inserted into proximal port 232, advanced along central lumen 230, and advanced through any one of distal port 234, first aperture 226 and second aperture 228.

FIG. 9C is a cross-section view of assembly 90 taken along section line C-C shown in FIG. 9A. With reference to FIG. 9C, it will be appreciated that re-entry device 100 may comprise a core wire 104 that is disposed in a central lumen 230 defined by shaft assembly 202 of orienting catheter 200. FIG. 9D is a cross-section view of assembly 90 taken along section line D-D shown in FIG. 9A. With reference to FIG. 9D, it will be appreciated that the distal portion of shaft assembly 202 defines a central lumen 230. Core wire 104 of re-entry device 100 can be seen residing in central lumen 230 in FIG. 9D.

FIG. 10 through FIG. 22 are a series of stylized pictorial views illustrating various steps that may be included as part of the methods in accordance with this detailed description. Methods and apparatus in accordance with the present detailed description may be used, for example, to establish a blood flow path around an occlusion in a blood vessel.

Figure 10:
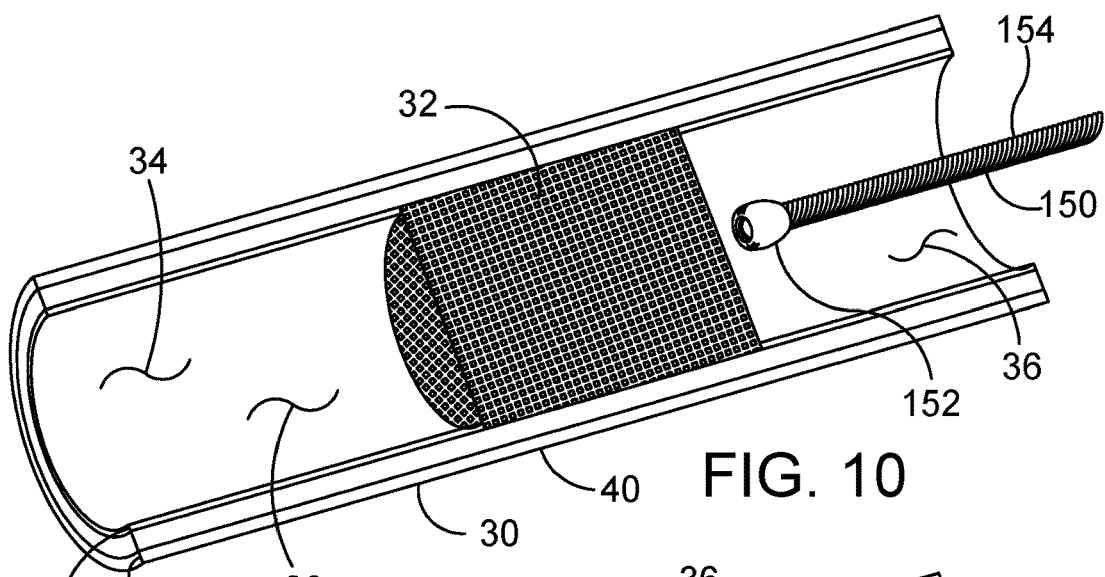

FIG. 10 is a longitudinal cross-sectional view of a blood vessel 30 having an occlusion 32 blocking the true lumen 34 thereof. Occlusion 32 divides true lumen 34 into a proximal lumen segment 36 and a distal lumen segment 38. In FIG. 10, a distal portion of a crossing device 150 is shown extending into proximal lumen segment 36 of true lumen 34. Crossing device 150 may be advanced over a guidewire to the position shown in FIG. 10. In the embodiment of FIG. 10, crossing device 150 comprises a tip 152 that is fixed to a distal end of a shaft 154. Tip 152 can be seen residing in proximal lumen segment 36 of true lumen 34 in FIG. 10.

Figure 11:
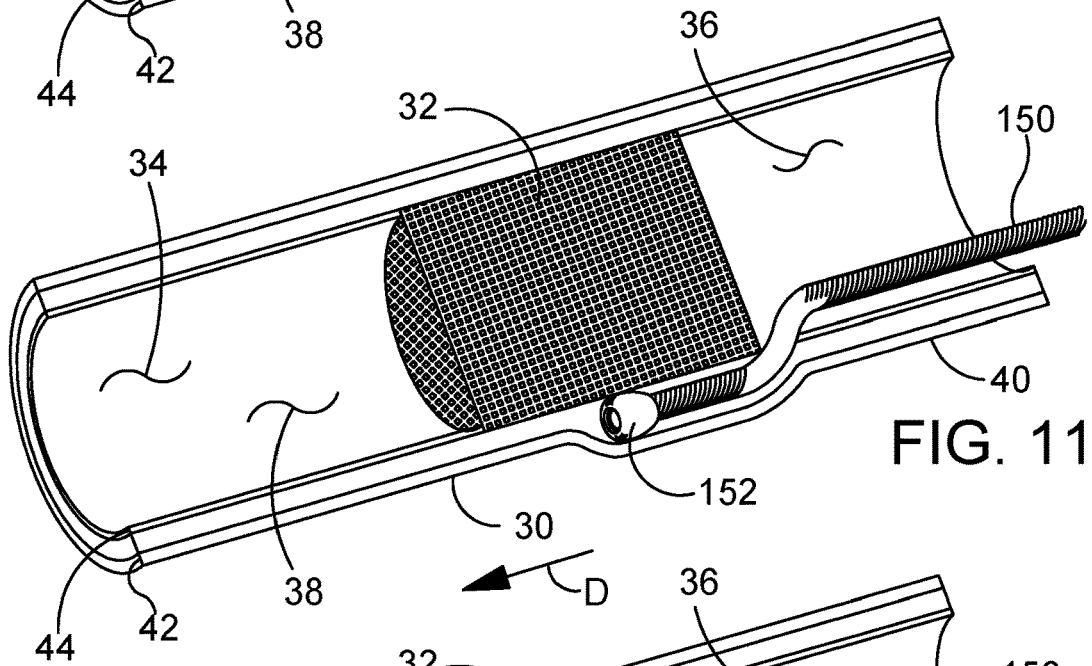

FIG. 11 is an additional longitudinal cross-sectional view of blood vessel 30. By comparing FIG. 11 with the previous figure, it will be appreciated that tip 152 of crossing device 150 has been advanced in a distal direction D. Distal direction D is illustrated using an arrow in FIG. 11. In the embodiment of FIG. 11, tip 152 of crossing device 150 is disposed in a position between occlusion 32 and adventitia 42 of blood vessel wall 40. Tip 152 is shown disposed adjacent occlusion 32 in FIG. 11. With reference to FIG. 11, it will be appreciated that crossing device 150 extends through intima 44 to the position between occlusion 32 and adventitia 42 of blood vessel 30.

Figure 12:
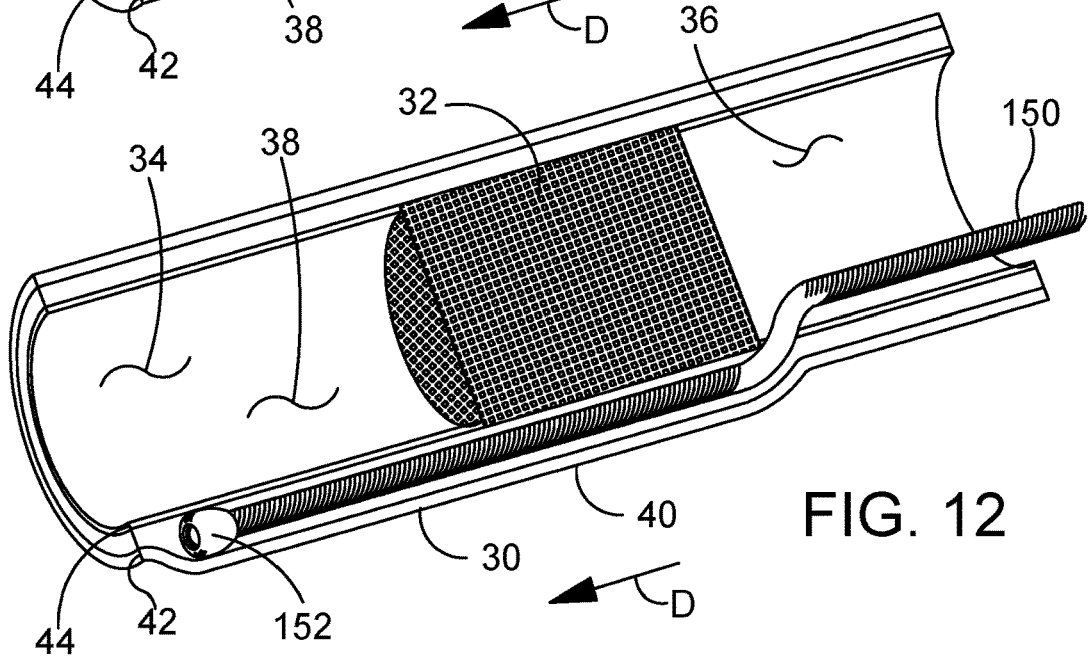

FIG. 12 is an additional view of blood vessel 30 and crossing device 150 shown in the previous figure. In the embodiment of FIG. 12, tip 152 of crossing device 150 has been advanced in distal direction D so that tip 152 is disposed at a location distal of occlusion 32. In the embodiment of FIG. 12, crossing device has moved in distal direction D between intima 44 and adventitia 42 as it has advanced distally beyond occlusion 32.

With reference to the sequence of three figures described immediately above, it will be appreciated that methods in accordance with the present detailed description may include the step of advancing a crossing device along a blood vessel to a location near an occlusion. The crossing device may be advanced over a guidewire that has been previously advanced to that location. These methods may also include the step of advancing the distal end of a crossing device (e.g., crossing device 150) between an occlusion and the adventitia of a blood vessel. The crossing device may be advanced beyond the occlusion to establish a blood flow path between a proximal segment on one side of the occlusion and a distal segment on the other side of the occlusion. For example, the crossing device may re-enter the lumen of the blood vessel as it moves past the occlusion. In some cases, the crossing device may advance distally between the intima and the adventitia of the blood vessel. As the tip of the crossing device moves in a distal direction between the intima and the adventitia, the tip may cause blunt dissection of the layers forming the wall of the blood vessel. If the tip of the crossing device does not spontaneously or automatically enter the lumen, a system in accordance with this detailed description may be used to pierce the intima and re-enter the lumen of the blood vessel.

In some useful methods in accordance with this detailed description, the crossing device may be rotated about its longitudinal axis and moved in a direction parallel to its longitudinal axis simultaneously. When this is the case, rotation of the crossing device may reduce resistance to the axial advancement of the crossing device. These methods take advantage of the fact that the kinetic coefficient of friction is usually less than the static coefficient of friction for a given frictional interface. Rotating the crossing device assures that the coefficient of friction at the interface between the crossing device and the surrounding tissue will be a kinetic coefficient of friction and not a static coefficient of friction. The rotating action may also change the direction of force vectors representing the effect of friction on the device.

Rotation of the crossing device can be achieved by rolling a handle portion of the crossing device between the thumb and forefinger of one hand, for example. Two hands may also be used to rotate the crossing device. In some useful methods in accordance with this detailed description, the crossing device is rotated at a rotational speed of between about 2 revolutions per minute and about 200 revolutions per minute. In some particularly useful methods in accordance with this detailed description, the crossing device is rotated at a rotational speed of between about 50 revolutions per minute and about 150 revolutions per minute. The crossing device may be rotated at a rotational speed that is sufficient to assure that the coefficient of friction at the interface between the crossing device and the surrounding tissue will be a kinetic coefficient of friction and not a static coefficient of friction. It is also contemplated that a mechanical device (e.g., an electric motor) may be used to rotate the crossing device.

FIG. 13 is an additional stylized pictorial view of blood vessel 30 and crossing device 150 shown in the previous figure. In the embodiment of FIG. 13, tip 152 of crossing device 150 is disposed at a location distal of occlusion 32. Tip 152 can be seen resting in an intrawall space S between the intima 44 and the adventitia 42 of blood vessel 30 in FIG. 13.

FIG. 14 is an additional stylized pictorial view of blood vessel 30 shown in the previous figure. By comparing FIG. 14 with the previous figure, it will be appreciated that a guidewire 999 may remain in the position formerly occupied by crossing device 150. With reference to FIG. 14, it will be appreciated that guidewire 999 may rest inside intrawall space S between the intima 44 and the adventitia 42 of blood vessel 30.

In the embodiment of FIG. 14, crossing device 150 has been withdrawn from blood vessel 30 while guidewire 999 has remained in the position shown in FIG. 14. The position of guidewire 999 shown in FIG. 14 may be achieved, for example, by first placing crossing device 150 in the position shown in the previous figure, then advancing guidewire 999 through a lumen defined by shaft 154 of crossing device 150. Alternately, guidewire 999 may be disposed within the lumen of shaft 154 while crossing device 150 is advanced beyond occlusion 32. With guidewire 999 in the position shown in FIG. 14, guidewire 999 may be used to direct other endovascular devices into the intrawall volume between occlusion 32 and adventitia 42. Examples of endovascular devices that may be advanced over guidewire 999 include balloon catheters, atherectomy catheters, and stent delivery catheters.

FIG. 15 is an additional stylized pictorial view of blood vessel 30 shown in the previous figure. In FIG. 15, an orienting catheter 200 is shown residing in the intrawall space previously occupied by guidewire 999. Orienting catheter 200 may be advanced into the position shown in FIG. 15, for example, by advancing orienting catheter 200 over guidewire 999 shown in the previous figure. Orienting catheter 200 comprises a shaft assembly 202 and an orienting element 204 that is carried by shaft assembly 202. Orienting element 204 may be capable of assuming both a collapsed shape and an expanded shape. Orienting element 204 may be selectively placed in the collapsed shape, for example, while the orienting element is being advanced past an occlusion (e.g., occlusion 32 shown in FIG. 15). Orienting element 204 may be selectively placed in the expanded shape, for example, while the orienting catheter 200 is being used to direct a re-entry device toward the lumen of a blood vessel. In FIG. 15, orienting element 204 is shown assuming the expanded shape.

Orienting element 204 of orienting catheter 200 comprises a first portion 206 and a second portion 208. In some instances, orienting element 204 may be an inflatable balloon. In the embodiment of FIG. 15, first portion 206 of orienting element 204 comprises a first inflatable member 220. Second portion 208 of orienting element 204 comprises a second inflatable member 224 in the embodiment of FIG. 15. First inflatable member 220 of orienting element 204 extends in a first direction 20 away from longitudinal axis 222 of shaft assembly 202. Second inflatable member 224 of orienting element 204 extends away from longitudinal axis 222 of shaft assembly 202 in a second direction 22 that is generally opposite the first direction. Shaft assembly 202 defines a distal port 234, a proximal port (not shown in FIG. 15) and a central lumen extending between the distal port and the proximal port.

Figure 16:
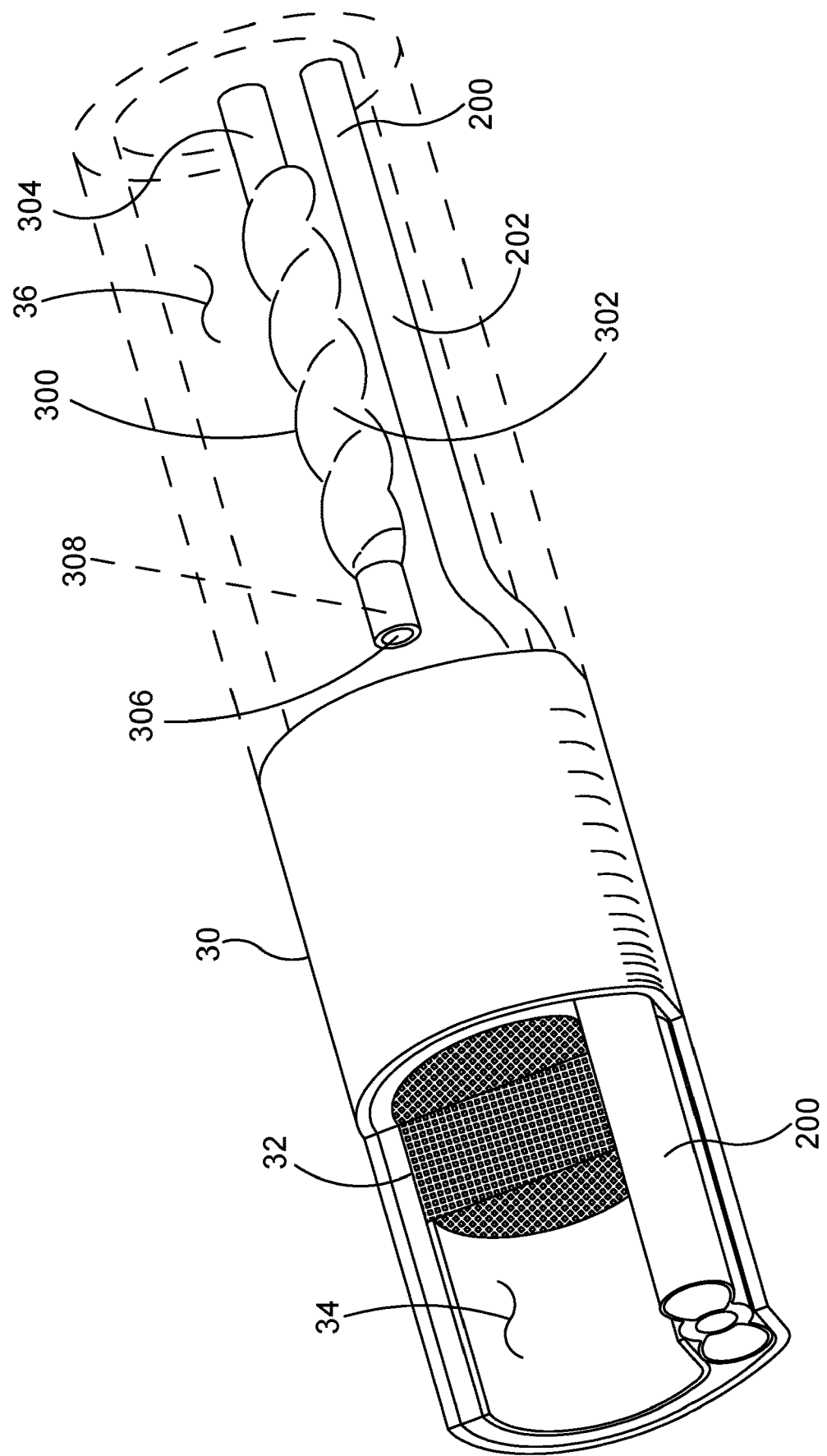

FIG. 16 is an additional stylized pictorial view of blood vessel 30 and orienting catheter 200 shown in the previous figure. In FIG. 16, a distal portion of an occlusion catheter 300 can be seen residing in proximal lumen segment 36 of true lumen 34. Occlusion catheter 300 includes a balloon 302 carried by a shaft assembly 304. Shaft assembly 304 defines an aspiration lumen 308 ending at a distal aspiration port 306. With reference to FIG. 16, it will be appreciated that balloon 302 of occlusion catheter 300 is disposed at a location slightly proximal of occlusion 32. In some cases, occlusion catheter 300 may be positioned by advancing it over a guidewire. In other cases, it may be desirable to use orientation catheter 200 as a guide. When this is the case, a tracking element may be coupled to both orienting catheter 200 and occlusion catheter 300. The tracking element may be adapted and configured to slide in distal and proximal axial directions along shaft assembly 202 of orienting catheter 200. The tracking element may be coupled to occlusion catheter 300 in a manner that precludes relative axial movement between shaft assembly 304 and the tracking element.

Figure 17:
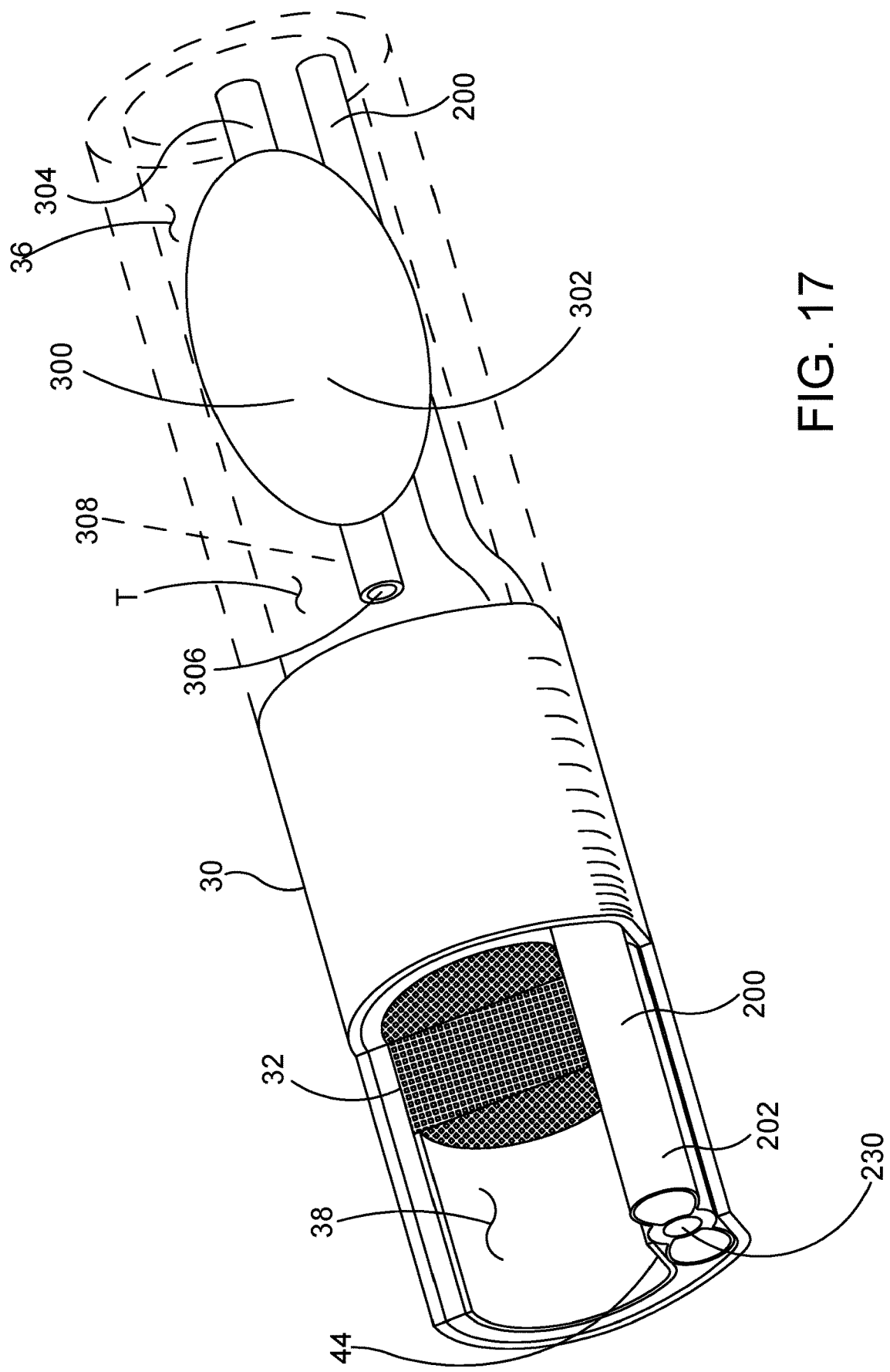

FIG. 17 is an additional stylized pictorial view of blood vessel 30 and occlusion catheter 300 shown in the previous figure. In FIG. 17, balloon 302 of occlusion catheter 300 is shown in an inflated state. In some useful embodiments, balloon 302 is adapted and dimensioned so as to occlude a blood vessel lumen when it assumes its inflated shape. In the embodiment of FIG. 17, balloon 302 has isolated a target volume T by occluding proximal lumen segment 36. The target volume T includes a portion of proximal lumen segment 36 extending between balloon 302 and occlusion 32 in the embodiment of FIG. 17. Target volume T also includes the intrawall space S occupied by orientation catheter 200.

With target volume T isolated, fluid may be withdrawn from the target volume T by drawing the fluid through distal aspiration port 306 and into aspiration lumen 308. Fluid may also be withdrawn from target volume T by drawing the fluid through central lumen 230 of orienting catheter 200. Withdrawing fluid from target volume T may reduce the pressure inside the target volume T (e.g., reduce the pressure inside the target volume T below ventral pressure PV) so that pressure inside distal lumen segment 38 presses the intima 44 of the blood vessel 30 against the orienting element 202 of orienting catheter 200. The pressure within the target volume T may be reduced to be less than the pressure within the distal lumen segment 38 (e.g., atrial pressure PA). Withdrawing fluid from the target volume may be particularly beneficial when the blood vessel wall has been dissected as one or more prolapsed guidewires, or other medical device, have passed through it. More particularly, withdrawing fluid from the target volume may facilitate the use of fluoroscopic imaging techniques when an elongated dissection is interfering with the flow of radiopaque imaging media into a lumen segment of the blood vessel. Additionally, withdrawing fluid from the intrawall space S may facilitate the piercing of intima 44 to complete a blood flow path extending between a proximal lumen segment and a distal lumen segment of the blood vessel.

Figure 18:
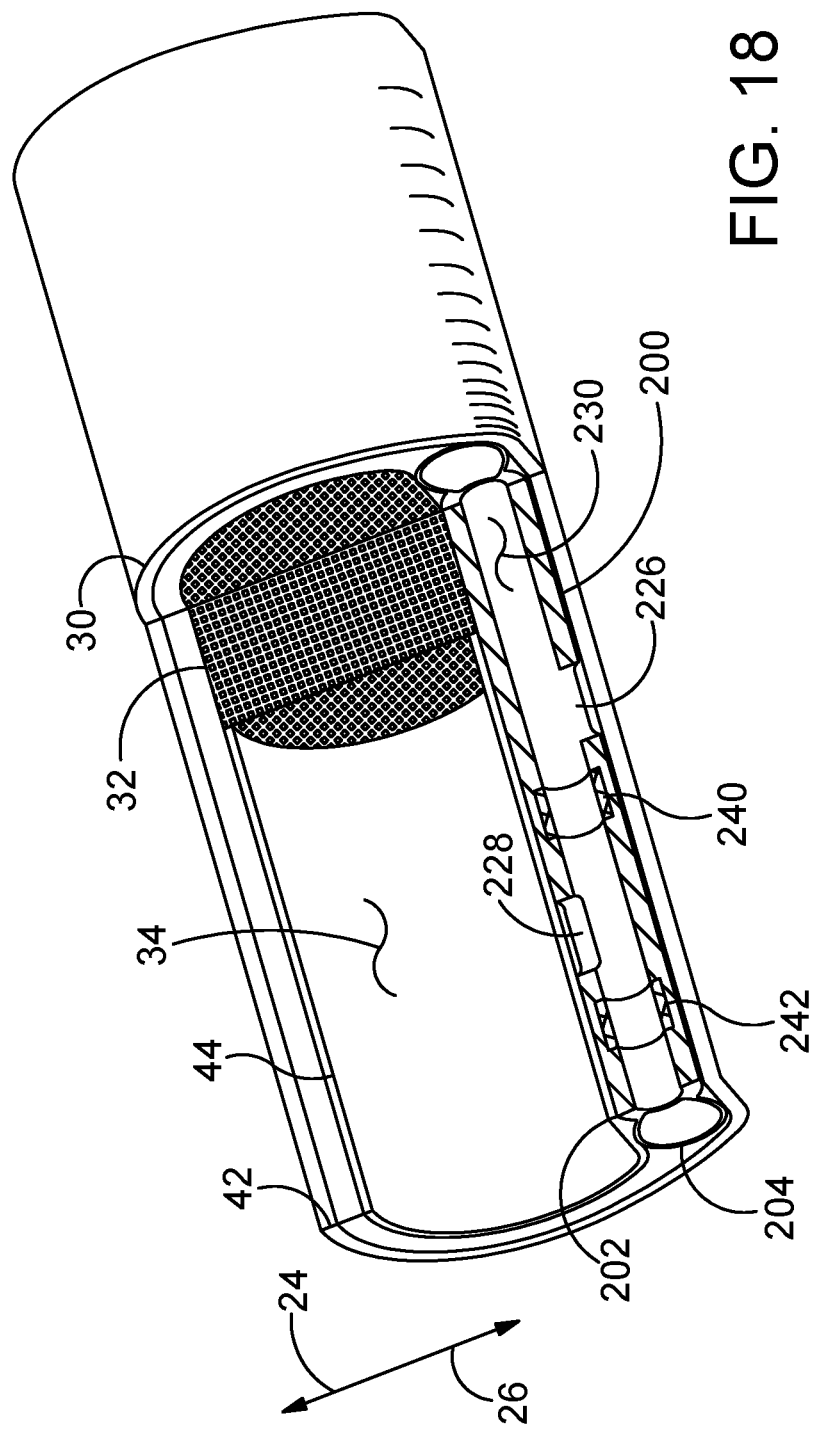

FIG. 18 is an additional stylized pictorial view of blood vessel 30 and orienting catheter 200 shown in the previous figure. For purposes of illustration, orienting catheter 200 is shown in cross-section in FIG. 18. With reference to FIG. 18, it will be appreciated that guidewire 999 has been withdrawn from a central lumen 230 of orienting catheter 200. Orienting catheter 200 comprises a shaft assembly 202 defining a first aperture 226 and a second aperture 228. In the embodiment of FIG. 18, first aperture 226 extends away from central lumen 230 in a third direction 24. Second aperture 228 extends away from central lumen 230 in a fourth direction 26 that is illustrated using an arrow in FIG. 18. Third direction 24 is also represented with an arrow in FIG. 18. In the embodiment of FIG. 18, third direction 24 and fourth direction 26 extend in generally opposite directions. In FIG. 18, the arrows representing third direction 24 and fourth direction 26 are directed about 180 degrees away from one another.

Orienting catheter 200 includes an orienting element 204, such as an orienting balloon, that is carried by shaft assembly 202. Orienting element 204 is shown assuming an expanded shape in FIG. 18. Orienting element 204 is also capable of assuming a collapsed shape. Orienting element 204 is dimensioned such that, when the orienting element assumes an expanded shape within the blood vessel wall, the shaft assembly will assume an arbitrary one of two possible orientations relative to the blood vessel lumen. The two possible orientations comprise a first orientation and a second orientation. In the exemplary embodiment of FIG. 18, first aperture 226 is positioned so as to open toward the blood vessel lumen when shaft assembly 202 is assuming the first orientation within the blood vessel wall. Second aperture 228 is positioned so as to open toward the blood vessel lumen when shaft assembly 202 is assuming the second orientation within the blood vessel wall. In the embodiment of FIG. 18 orienting catheter 200 is oriented so that second aperture 228 opens toward intima 44 of blood vessel 30 and first aperture 226 opens away from intima 44. Therefore, it will be appreciated that orienting device is assuming the second orientation.

In the embodiment of FIG. 18, first aperture 226 and second aperture 228 are longitudinally separated from one another, although other configurations are contemplated. Orienting catheter 200 includes a first radiopaque marker 240 that is located between first aperture 226 and second aperture 228. A second radiopaque marker 242 of orienting catheter 200 is located distally of second aperture 228.

In FIG. 18, an occlusion 32 is shown blocking lumen 34 of blood vessel 30. Occlusion 32 prevents blood from flowing through blood vessel 30. Fluid communication between a proximal segment of blood vessel lumen 34 and a distal segment of blood vessel lumen 34 may be achieved by re-entering the lumen with a re-entry device. Orienting catheter 200 may be used to direct the re-entry device toward true lumen 34 to complete a blood flow path extending around occlusion 32.

FIG. 19 is an additional stylized pictorial view of blood vessel 30 and orienting catheter 200 shown in the previous figure. In the embodiment of FIG. 19, a re-entry device 100 has been advanced into central lumen 230 of orienting catheter 200. With reference to FIG. 19, it will be appreciated that re-entry device 100 may include a bend 142. In the embodiment of FIG. 19, re-entry device 100 is biased to assume a bent shape. Also in the embodiment of FIG. 19, the wall of shaft assembly 202 is holding re-entry device 100 in a somewhat deflected state. When this is the case, re-entry device 100 can be inserted through second aperture 228 by positioning the distal end of re-entry device 100 over second aperture 228 and allowing bend 142 to assume it's natural state (i.e., bent at a sharper angle). In the embodiment of FIG. 19, rotating re-entry device 100 within central lumen 230 of orienting catheter 200 will cause the distal end of re-entry device 100 to enter second aperture 228.

A physician may use a fluoroscopic display for guidance when placing the distal end of the re-entry device 100 in general alignment with a selected aperture. When using fluoroscopic guidance, re-entry device 100, first radiopaque marker 240, and second radiopaque marker 242 will all be brightly displayed by the fluoroscopy system. When the physician positions the distal end of re-entry device 100 slightly proximal of first radiopaque marker 240, the physician may infer that the distal end of re-entry device 100 is at a longitudinal position (i.e., a position along longitudinal axis 222) that is in general alignment with first aperture 226. The physician may then rotate re-entry device 100 so that the distal end of re-entry device 100 enters first aperture 226. The distal end of re-entry device 100 may then be advanced through first aperture 226. The physician may observe the direction that a distal portion of re-entry device 100 travels as it passes through first aperture 226. From these fluoroscopic observations, the physician can determine whether the distal end of the re-entry device 100 is directed toward the vascular lumen or directed away from the vascular lumen. If it is determined that the re-entry device 100 is directed toward the vascular lumen, then the re-entry device 100 can be advanced so that the distal end of re-entry device 100 travels through the intima to a position inside the lumen 34 of blood vessel 30. If it is determined that the re-entry device 100 is directed away from the vascular lumen, then the re-entry device 100 can be withdrawn from first aperture 226 so that the re-entry device 100 is again located within orienting catheter 200. At this point, the physician may determine second aperture 228 should be used for re-entry on this particular occasion.

When the physician positions the distal end of re-entry device 100 between first radiopaque marker 240 and second radiopaque marker 242, the physician may infer that the distal end of re-entry device 100 is at a longitudinal position (i.e., a position along longitudinal axis 222) that is in general alignment with second aperture 228. The physician may then rotate re-entry device 100 so that the distal end of re-entry device 100 enters second aperture 228. The distal end of re-entry device 100 may then be advanced through second aperture 228. The physician may observe the direction that a distal portion of re-entry device 100 travels as it passes through second aperture 228. From these fluoroscopic observations, the physician can confirm that the distal end of the re-entry device 100 is directed toward the vascular lumen 34. If it is confirmed that the re-entry device 100 is directed toward the vascular lumen 34, then the re-entry device 100 can be advanced so that the distal end of re-entry device 100 travels through the intima 44 to a position inside the lumen 34 of blood vessel 30. It is contemplated that other structures/configurations may be utilized to cause/allow the re-entry device 100 to pass from the orienting catheter 200 for re-entry into the vascular lumen 34.

FIG. 20 is an additional stylized pictorial view showing re-entry device 100 and orienting catheter 200 shown in the previous figure. By comparing FIG. 20 and the previous figure, it will be appreciated that re-entry device 100 has been rotated so that a distal portion of re-entry device 100 has entered second aperture 228. With reference to FIG. 20, it will be appreciated that re-entry device 100 may comprise a distal surface 108 and a probe 106 extending beyond distal surface 108. In the embodiment of FIG. 20, probe 106 of re-entry device 100 is contacting intima 44 of blood vessel 30. Re-entry device 100 is shown extending distally through central lumen 230 and second aperture 228 in the embodiment of FIG. 20. By advancing re-entry device 100 further in the distal direction D, re-entry device 100 can be advanced through second aperture 228 and through intima 44.

FIG. 21 is an additional stylized pictorial view showing re-entry device 100 and orienting catheter 200 shown in the previous figure. In the embodiment of FIG. 21, re-entry device 100 has been advanced further in distal direction D and probe 106 of re-entry device 100 has pierced the surface of intima 44. Probe 106 can be seen extending into intima 44 in FIG. 21. Intima 44 may be weakened when pierced by probe 106 as shown in FIG. 21. Probe 106 may also function to anchor the distal tip of re-entry device 100 to intima 44 so that the distal tip is less likely to slide along the intima 44 when pushing forces are applied to the proximal end of re-entry device 100. The anchoring and weakening functions described above may aid a physician in advancing re-entry device 100 through intima 44.

FIG. 22 is an additional stylized pictorial view showing re-entry device 100 and orienting catheter 200 shown in the previous figure. In the embodiment of FIG. 22, a distal portion of re-entry device 100 has been advanced through intima 44. With reference to FIG. 22, it will be appreciated that distal surface 108 of re-entry device 100 is disposed in the lumen 34 of blood vessel 30. Probe 106 of re-entry device 100 can be seen extending beyond distal surface 108. Re-entry device 100 has pierced intima 44 creating a hole extending through the intima 44. A blood flow path extending around occlusion 32 is completed when re-entry device 100 pierces intima 44.

Figure 23:
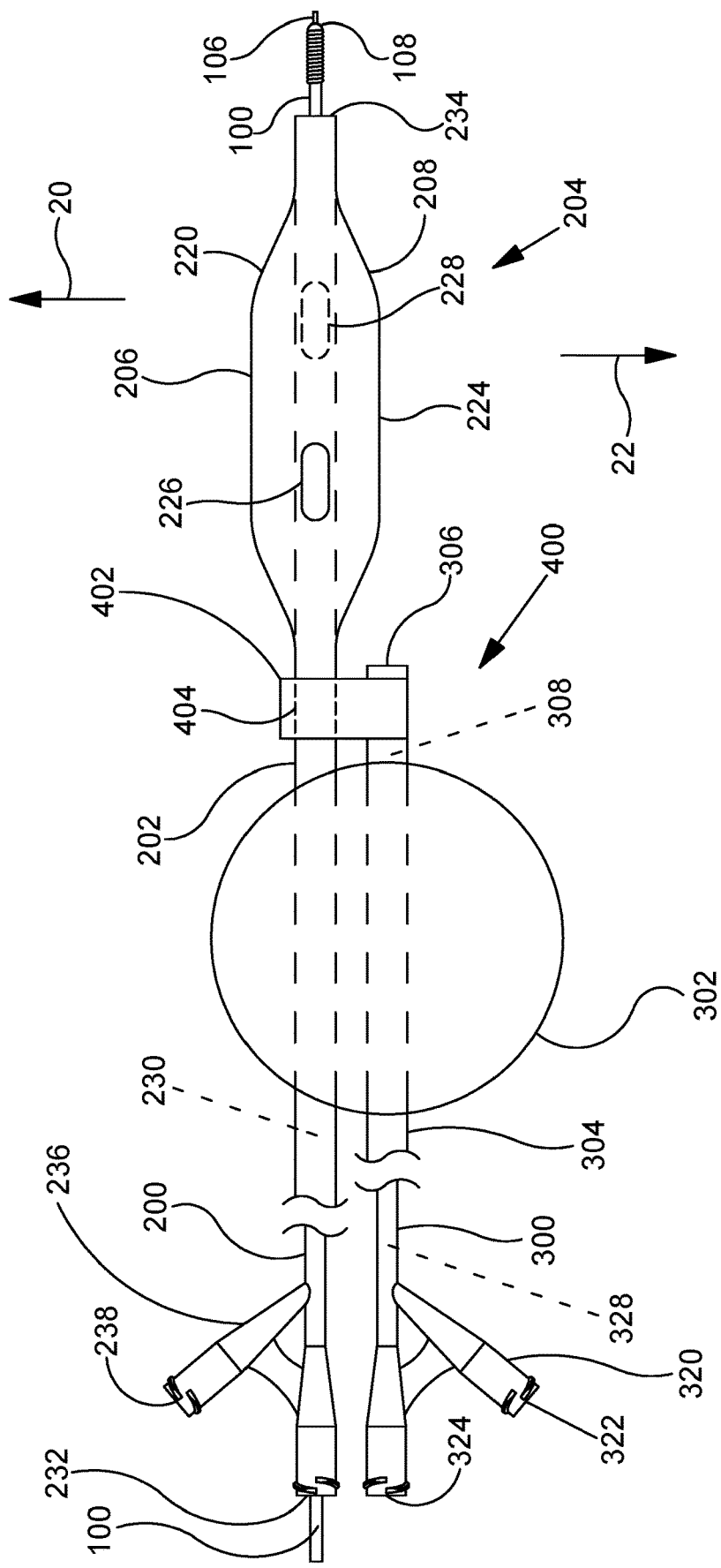
FIG. 23 is a plan view showing a system that may be useful, for example, when establishing a blood flow path between a proximal segment of a blood vessel and a distal segment of a blood vessel that are separated by an occlusion. The system of FIG. 23 may also be used to facilitate visualization of a patient's vasculature using fluoroscopic techniques when conditions arise which interfere with the flow of radiopaque media.

FIG. 23 is a plan view showing a system 400 in accordance with the present detailed description. System 400 of FIG. 23 may be useful, for example, when establishing a blood flow path between a proximal segment of a blood vessel and a distal segment of a blood vessel that are separated by an occlusion (e.g., the subject matter illustrated in the preceding series of figures). System 400 may also be used to facilitate visualization of a patient's vasculature using fluoroscopic techniques when conditions arise which interfere with the flow of radiopaque media.

Orienting catheter 200 of FIG. 23 comprises a shaft assembly 202 and an orienting element 204, such as an orienting balloon, that is carried by shaft assembly 202. Orienting element 204 is capable of assuming both a collapsed shape and an expanded shape. Orienting element 204 may be selectively placed in the collapsed shape, for example, while the orienting element 204 is being advanced past an occlusion. Orienting element 204 may be selectively placed in the expanded shape, for example, while the orienting catheter 200 is being used to direct re-entry device 100 toward the lumen of a blood vessel. In FIG. 23, orienting element 204 is shown assuming the expanded shape.

Orienting element 204 of orienting catheter 200 comprises a first portion 206 and a second portion 208. In the embodiment of FIG. 23, first portion 206 of orienting element 204 comprises a first inflatable member 220. Second portion 208 of orienting element 204 comprises a second inflatable member 224 in the embodiment of FIG. 23. First inflatable member 220 of orienting element 204 extends in a first direction 20 away from the longitudinal axis of shaft assembly 202. Second inflatable member 224 of orienting element 204 extends away from the longitudinal axis of shaft assembly 202 in a second direction 22. First direction 20 and second direction 22 are represented with arrows in FIG. 23. With reference to FIG. 23, it will be appreciated that second direction 22 is generally opposite first direction 20. In FIG. 23, the arrows representing first direction 20 and second direction 22 are directed about 180 degrees away from one another.

Shaft assembly 202 of FIG. 23 defines a first aperture 226 and a second aperture 228. In the embodiment of FIG. 23, first aperture 226 extends away from central lumen 230 in a third direction that is generally perpendicular to first direction 20 and second direction 22. Second aperture 228 extends away from central lumen 230 in a fourth direction that is generally perpendicular to first direction 20 and second direction 22. In the embodiment of FIG. 23, the fourth direction is generally opposite to the third direction. In other words, the third direction and the fourth direction are directed about 180 degrees away from each other. The third direction and the fourth direction are both generally orthogonal to the picture plane that the plan view of FIG. 23 is displayed on. It is contemplated that in other embodiments the first and second apertures 226, 228 may have a different orientation.

A hub 236 is fixed to the proximal end of shaft assembly 202. Hub 236 includes an inflation port 238. Inflation port 238 fluidly communicates with the interior of first inflatable member 220 and second inflatable member 224 via inflation lumens defined by shaft assembly 202. The inflatable members 220, 224 may be inflated by injecting an inflation media into inflation port 238. Examples of inflation media that may be suitable in some applications include saline, carbon dioxide, and nitrogen.

Orienting catheter 200 defines a proximal port 232, a distal port 234 and a central lumen 230 that extends between proximal port 232 and distal port 234. In the embodiment of FIG. 23, proximal port 232 is defined by hub 236 and distal port 234 is defined by shaft assembly 202. In FIG. 23, re-entry device 100 can be seen extending through proximal port 232, central lumen 230, and distal port 234. With reference to FIG. 23, it will be appreciated that re-entry device 100 comprises a distal surface 108 and a probe 106 extending beyond distal surface 108. Re-entry device 100 may be inserted into proximal port 232, advanced along central lumen 230, and advanced through any one of distal port 234, first aperture 226 and second aperture 228.

System 400 of FIG. 23 includes an occlusion catheter 300, an orienting catheter 200 and re-entry device 100. Occlusion catheter 300 includes a balloon 302 carried by a shaft assembly 304. A hub 320 is fixed to the proximal end of shaft assembly 304. Hub 320 defines an inflation port 322 and a proximal aspiration port 324. Shaft assembly 304 of occlusion catheter 300 defines an inflation lumen 328 and an aspiration lumen 308 that fluidly communicate with inflation port 322 and proximal aspiration port 324, respectively. Aspiration lumen 308 extends between proximal aspiration port 324 and a distal aspiration port 306. Inflation lumen 328 extends between inflation port 322 and the interior of balloon 302.

In FIG. 23, balloon 302 is shown assuming an inflated shape. Balloon 302 can be selectively inflated by injecting an inflation fluid into balloon 302 via inflation port 322 and inflation lumen 328. In some useful embodiments, balloon 302 is adapted and dimensioned so as to occlude a blood vessel lumen when it assumes the inflated shape. Balloon 302 may be used to isolate a target volume by occluding the true lumen of the blood vessel. The target volume may include an intrawall space located between the intima and the adventitia of the blood vessel. The target volume may also include a portion of the lumen extending between the balloon and an occlusion that is blocking the lumen of the blood vessel. With the target volume isolated, fluid may be withdrawn from it by drawing the fluid through distal aspiration port 306 and aspiration lumen 308 of occlusion catheter 300. Fluid may also be withdrawn from target volume T by drawing the fluid through central lumen 230 of orienting catheter 200.

System 400 includes a tracking element 402 defining a tracking element lumen 404. Shaft assembly 202 of orienting catheter 200 can be seen extending through tracking element lumen 404 in FIG. 23. Tracking element lumen 404 is configured so that tracking element 402 is free to slide in distal and proximal axial directions along shaft assembly 202 of orienting catheter 200. Occlusion catheter 300 is connected to tracking element 402 so that axial movement between tracking element 400 and occlusion catheter 300 is precluded.

FIG. 24A is a plan view showing a system 400 in accordance with the present detailed description. FIG. 24B is an enlarged plan view further illustrating a portion of system 400. FIG. 24A and FIG. 24B may be collectively referred to as FIG. 24. System 400 of FIG. 24 includes an occlusion catheter 300, an orienting catheter 200 and a re-entry device 100. Orienting catheter 200 comprises an orienting element 204 carried by a shaft assembly 202. Occlusion catheter 300 comprises a balloon 302 carried by a shaft assembly 304.

Shaft assembly 202 of orienting catheter 200 defines a first aperture 226, a second aperture 228, a distal port 234 and a central lumen 230. Central lumen 230 extends between distal port 234 and a proximal port 232 is defined by a hub 236. In FIG. 24, re-entry device 100 can be seen extending through proximal port 232, central lumen 230, and distal port 234. Re-entry device 100 may be inserted into proximal port 232, advanced along central lumen 230, and advanced through any one of distal port 234, first aperture 226 and second aperture 228. With reference to FIG. 24, it will be appreciated that re-entry device 100 comprises a distal surface 108 and a probe 106 extending beyond distal surface 108.

Orienting element 204 of orienting catheter 200 comprises a first portion 206 and a second portion 208. In the embodiment of FIG. 24, first portion 206 of orienting element 204 comprises a first inflatable member 220. Second portion 208 of orienting element 204 comprises a second inflatable member 224 in the embodiment of FIG. 24. Shaft assembly 202 defines inflation lumens that fluidly communicate with the interior of first inflatable member 220, the interior of second inflatable member 224, and inflation port 238 defined by hub 236. The inflatable members may be inflated by injecting an inflation media into inflation port 238.

A hub 320 is fixed to the proximal end of shaft assembly 304 of occlusion catheter 300. Hub 320 defines an inflation port 322 and a proximal aspiration port 324. Shaft assembly 304 of occlusion catheter 300 defines an inflation lumen 328 and an aspiration lumen 308 that fluidly communicate with inflation port 322 and proximal aspiration port 324, respectively. Aspiration lumen 308 extends between proximal aspiration port 324 and a distal aspiration port 306. Inflation lumen 328 extends between inflation port 322 and the interior of balloon 302.

In FIG. 24, balloon 302 is shown assuming a collapsed and folded state. Balloon 302 can be selectively inflated by injecting an inflation fluid into balloon 302 via inflation port 322 and inflation lumen 328. In some useful embodiments, balloon 302 is adapted and dimensioned so as to occlude a blood vessel lumen when it assumes the inflated shape. Balloon 302 may be used to isolate a target volume by occluding a lumen segment of a blood vessel. The target volume may include an intrawall space located between the intima and the adventitia of the blood vessel. The target volume may also include a portion of the lumen segment extending between the balloon 302 and an occlusion that is blocking the lumen of the blood vessel. With the target volume isolated, fluid may be withdrawn from it by drawing the fluid through distal aspiration port 306 and into aspiration lumen 308. Fluid may also be withdrawn from the target volume by drawing the fluid through central lumen 230 of orienting catheter 200 if desired.

System 400 includes a tracking element 402 defining a tracking element lumen 404. Shaft assembly 202 of orienting catheter 200 can be seen extending through tracking element lumen 404 in FIG. 24. Tracking element lumen 404 is configured so that tracking element 402 is free to slide in distal and proximal axial directions along shaft assembly 202 of orienting catheter 200. Occlusion catheter 300 and tracking element 402 comprise a male coupling element 408 and a female coupling element 406, respectively. Male coupling element 408 and female coupling element 406 are adapted and configured to cooperatively form a mechanical connection between occlusion catheter 300 and tracking element 402. In some useful embodiments, this connection is adapted and configured so that axial movement between tracking element 400 and occlusion catheter 300 is precluded. In the embodiment of FIG. 24, male coupling element 408 includes a shoulder 420 having a proximal facing surface 424. Female coupling element 406 comprises two tangs 426 in the embodiment of FIG. 24. In other embodiments, the female coupling element 406 and the male coupling element 408 may be reversed, with the female coupling element 406 provided on the occlusion catheter 300 and the male coupling element 408 provided on the tracking element 402.

FIG. 25A is an additional plan view further illustrating system 400 shown in the previous figure. FIG. 25B is an enlarged plan view further illustrating a portion of system 400. In the embodiment of FIG. 25, male coupling element 408 of occlusion catheter 300 and female coupling element 406 of orienting catheter 200 are cooperating to form a connection 440. Connection 440 is adapted and configured so that axial movement between tracking element 400 and occlusion catheter 300 is precluded in the embodiment of FIG. 25. A proximal edge of each tang 426 can be seen contacting the proximal-facing surface of the shoulder 420 in FIG. 25B.

FIG. 26A is a plan view showing a system 400 in accordance with the present detailed description. FIG. 26B is an enlarged plan view further illustrating a portion of system 400. FIG. 26A and FIG. 26B may be collectively referred to as FIG. 26. System 400 may be useful, for example, when establishing a blood flow path between a proximal segment of a blood vessel and a distal segment of a blood vessel that are separated by an occlusion (e.g., the subject matter illustrated in the preceding series of figures). System 400 may also be useful to facilitate visualization of a patient's vasculature using fluoroscopic techniques when conditions arise which interfere with the flow of radiopaque media.

System 400 of FIG. 26 includes an occlusion catheter 300, an orienting catheter 200 and re-entry device 100. Orienting catheter 200 of FIG. 26 comprises a shaft assembly 202 and an orienting element 204 that is carried by shaft assembly 202. Orienting element 204 of orienting catheter 200 comprises a first portion 206 and a second portion 208. In the embodiment of FIG. 26, first portion 206 of orienting element 204 comprises a first inflatable member 220. Second portion 208 of orienting element 204 comprises a second inflatable member 224 in the embodiment of FIG. 26. The inflatable members may be inflated by injecting an inflation media into them via inflation lumens defined by shaft assembly 202. The interior of first inflatable member 220 and the interior of second inflatable member 224 fluidly communicate with an inflation port 238 defined by a hub 236.

Orienting catheter 200 defines a proximal port 232, a distal port 234 and a central lumen 230 that extends between proximal port 232 and distal port 234. In the embodiment of FIG. 26, proximal port 232 is defined by hub 236 and distal port 234 is defined by shaft assembly 202. Shaft assembly 202 of orienting catheter 200 defines a first aperture 226 and a second aperture 228. In FIG. 26, re-entry device 100 can be seen extending through proximal port 232, central lumen 230, and distal port 234. With reference to FIG. 26, it will be appreciated that re-entry device 100 comprises a distal surface 108 and a probe 106 extending beyond distal surface 108. Re-entry device 100 may be inserted into proximal port 232, advanced along central lumen 230, and advanced through any one of distal port 234, first aperture 226 and second aperture 228.

Occlusion catheter 300 of system 400 comprises a balloon 302 carried by a shaft assembly 304. A hub 320 is fixed to the proximal end of shaft assembly 304 of occlusion catheter 300. Hub 320 defines an inflation port 322 and a proximal aspiration port 324. Shaft assembly 304 of occlusion catheter 300 defines an inflation lumen 328 and an aspiration lumen 308 that fluidly communicate with inflation port 322 and proximal aspiration port 324, respectively. Aspiration lumen 308 extends between proximal aspiration port 324 and a distal aspiration port 306. Inflation lumen 328 extends between inflation port 322 and the interior of balloon 302.

In FIG. 26, balloon 302 is shown assuming a collapsed and folded state. Balloon 302 can be selectively inflated by injecting an inflation fluid into balloon 302 via inflation port 322 and inflation lumen 328. In some useful embodiments, balloon 302 is adapted and dimensioned so as to occlude a blood vessel lumen when it assumes the inflated shape. Balloon 302 may be used to isolate a target volume by occluding a lumen segment of a blood vessel. The target volume may include an intrawall space located between the intima and the adventitia of the blood vessel. The target volume may also include a portion of the lumen segment extending between the balloon and an occlusion that is blocking the lumen of the blood vessel. With the target volume isolated, fluid may be withdrawn from it by drawing the fluid through distal aspiration port 306 and into aspiration lumen 308. Fluid may also be withdrawn from the target volume by drawing the fluid through central lumen 230 of orienting catheter 200 if desired.

System 400 includes a tracking element 402 defining a tracking element lumen 404. Shaft assembly 202 of orienting catheter 200 can be seen extending through tracking element lumen 404 in FIG. 26. Tracking element lumen 404 is configured so that tracking element 402 is free to slide in distal and proximal axial directions along shaft assembly 202 of orienting catheter 200. Occlusion catheter 300 and tracking element 402 comprise a male coupling element 408 and a female coupling element 406, respectively. Male coupling element 408 and female coupling element 406 are adapted and configured to cooperatively form a mechanical connection between occlusion catheter 300 and tracking element 402. In some useful embodiments, this connection is adapted and configured so that axial movement between tracking element 400 and occlusion catheter 300 is precluded. In the embodiment of FIG. 26, female coupling element 406 includes a shoulder 420 having a distal facing surface 422. Male coupling element 408 comprises two fingers 428 in the embodiment of FIG. 26. In other embodiments, the female coupling element 406 and the male coupling element 408 may be reversed, with the female coupling element 406 provided on the occlusion catheter 300 and the male coupling element 408 provided on the tracking element 402.

Figure 27A:
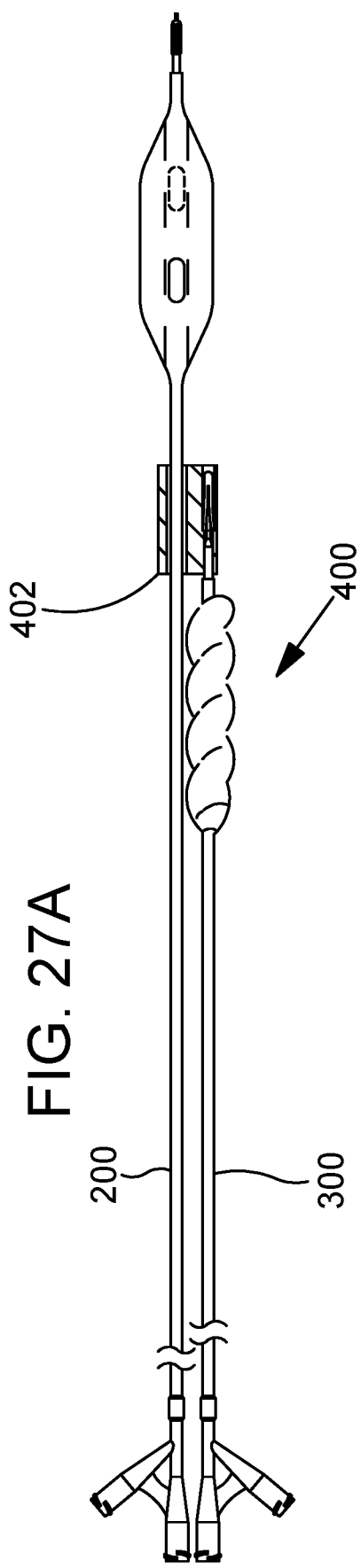
FIG. 27A is an additional plan view illustrating a second configuration of the system shown in FIGS. 26A-26B.
Figure 27B:
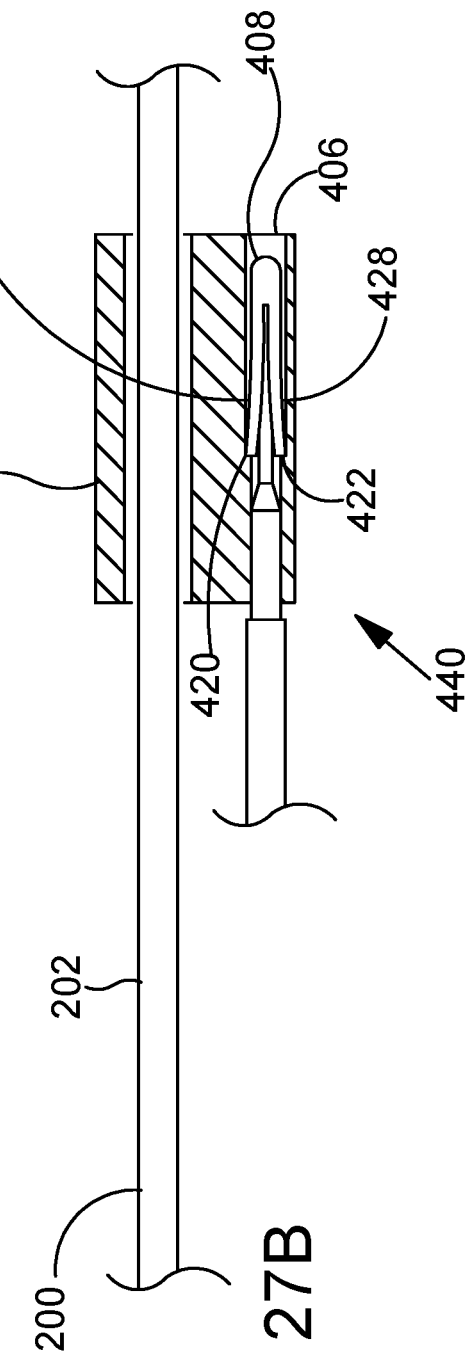
FIG. 27B is an enlarged plan view further illustrating a portion of the system shown in FIG. 27A.

FIG. 27A is an additional plan view further illustrating system 400 shown in the previous figure. FIG. 27B is an enlarged plan view further illustrating a portion of system 400. Male coupling element 408 of occlusion catheter 300 and female coupling element 406 of orienting catheter 200 are cooperating to form a connection 440 in the embodiment of FIG. 27. In the embodiment of FIG. 27, this connection is adapted and configured so that axial movement between tracking element 400 and occlusion catheter 300 is precluded. A proximal edge of each finger 428 can be seen contacting the distal-facing surface 422 of the shoulder in FIG. 27B.

FIG. 28A is a stylized pictorial view of a blood vessel 30 having a wall 40 including an adventitia 42, a media M, and an intima 44. In the embodiment of FIG. 28A, an orienting element 202 of an orienting catheter 200 is disposed in an intrawall space S located between the intima 44 and the adventitia 42 of blood vessel 30. In the embodiment of FIG. 28A, a portion of intima 44 has become separated from the other layers of blood vessel wall 40. This situation may occur, for example, when a physician has passed one or more prolapsed guidewires between the intima and the adventitia.

FIG. 28B is an additional stylized pictorial view of blood vessel 30 shown in the previous figure. By comparing FIG. 28B with FIG. 28A, it will be appreciated that the volume of intrawall space S has been reduced substantially. Intima 44 can be seen contacting orienting element 202 of orienting catheter 200 in FIG. 28B. In some useful methods, the volume of an intrawall space S may be reduced by withdrawing fluid from the intrawall space. Fluid may be withdrawn from intrawall space S by drawing the fluid through central lumen 230 of orienting catheter 200. Fluid may also be withdrawn from intrawall space S by drawing the fluid through the aspiration lumen of an occlusion catheter 300 in accordance with this detailed description.

Withdrawing fluid from intrawall space S may reduce the pressure inside the intrawall space S to a pressure less than the pressure in the true lumen distal of the occlusion (e.g., below atrial pressure PA) so that pressure inside the true lumen distal of the occlusion presses the intima 44 of the blood vessel 30 against the orienting element 202 of the orienting catheter 200. In other words, the pressure on the intrawall side of the intima 44 may be less than the pressure on the true lumen side of the intima 44 distal of the occlusion. Withdrawing fluid from the intrawall space S may be particularly beneficial when the blood vessel wall has been dissected as one or more prolapsed guidewires have passed through it. More particularly, withdrawing fluid from the intrawall space S may facilitate the use of fluoroscopic imaging techniques when an elongated dissection is interfering with the flow of radiopaque imaging media into a lumen segment of the blood vessel. Additionally, withdrawing fluid from the intrawall space S may facilitate the piercing of intima 44 to complete a blood flow path extending between a proximal lumen segment and a distal lumen segment of the blood vessel.

From the foregoing, it will be apparent to those skilled in the art that the present disclosure provides, in exemplary non-limiting embodiments, devices and methods for the treatment of chronic total occlusions. Further, those skilled in the art will recognize that aspects of the present disclosure may be manifested in a variety of forms other than the specific embodiments described and contemplated herein. Accordingly, departures in form and detail may be made without departing from the scope and spirit of the present disclosure as described in the appended claims.

What is claimed is:

1. A method for treating a blood vessel including a blood vessel wall defining a blood vessel lumen, the blood vessel lumen being at least partially obstructed by an occlusion, the occlusion dividing the lumen into a proximal lumen segment and a distal lumen segment, the method comprising:
    positioning an orienting element of an orienting catheter inside an intrawall space located distal of the occlusion from the proximal lumen segment, the intrawall space being located between an intima and an adventitia of the blood vessel wall;
    positioning an occluding element of an occlusion catheter in the proximal lumen segment at a location near the occlusion, the occluding element comprising a balloon;
    inflating the balloon of the occlusion catheter in the proximal lumen segment so as to isolate a target volume, the target volume including the intrawall space;
    reducing a pressure inside the target volume, wherein a pressure inside the intrawall space is greater than a pressure in the distal lumen segment before the pressure inside the target volume is reduced, and the pressure inside the intrawall space is less than the pressure in the distal lumen segment after the pressure inside the target volume is reduced;
    deploying the orienting element in the intrawall space so that the orienting catheter assumes an orientation in which a port of the orienting catheter is directed toward the distal lumen segment; and
    advancing a distal end of a reentry device from the port through the intima and into the distal lumen segment.

2. The method of claim 1, wherein reducing the pressure inside the target volume comprises placing a vacuum source in fluid communication with the target volume via a lumen defined by the orienting catheter or via a lumen defined by the occlusion catheter.

3. The method of claim 1, wherein reducing the pressure inside the target volume comprises placing a source of low pressure in fluid communication with the target volume via a lumen defined by the orienting catheter or via a lumen defined by the occlusion catheter.

4. The method of claim 1, wherein reducing the pressure inside the target volume comprises placing a lumen of the occlusion catheter or a lumen of the orienting catheter in fluid communication with the target volume.

5. The method of claim 1, wherein reducing the pressure inside the target volume comprises withdrawing fluid from the target volume via a lumen defined by the orienting catheter or via a lumen defined by the occlusion catheter.

6. The method of claim 1, wherein:
    the orienting catheter comprises a central lumen and a first port in fluid communication with the central lumen; and
    deploying the orienting element causes the orienting catheter to assume an arbitrary one of two possible orientations relative to the distal lumen segment, the two possible orientations comprising a first orientation in which the first port is directed toward the distal lumen segment and a second orientation in which the first port is directed about 180 degrees away from the distal lumen segment.

7. The method of claim 1, wherein:
    the orienting catheter comprises a central lumen, a first port and a second port, the first and second ports both being in fluid communication with the central lumen; and
    deploying the orienting element while the intima is pressing thereagainst causes the orienting catheter to assume an arbitrary one of two possible orientations relative to the distal lumen segment, the two possible orientations comprising a first orientation in which the first port is directed toward the distal lumen segment and a second orientation in which the second port is directed toward the distal lumen segment.

8. The method of claim 1, wherein a pressure in the distal lumen segment presses the intima against the orienting element of the orienting catheter while a pressure inside the intrawall space is less than the pressure in the distal lumen segment.

9. The method of claim 1, wherein:
    the occlusion catheter comprises a tracking element carried by a shaft; and
    the method comprises forming a sliding connection between the occlusion catheter and the orienting catheter with the tracking element.

10. The method of claim 1, wherein:
    the occlusion catheter comprises a tracking element carried by a shaft; and
    the method comprises advancing the tracking element in an axial direction along the orienting catheter while the occlusion catheter remains outside of and positioned along side the orienting catheter.

11. The method of claim 1, further comprising:
    advancing the distal end of a crossing device between the occlusion and the adventitia of the blood vessel wall; and
    advancing the distal end of the crossing device distally beyond the occlusion to form a tunnel between the intima and the adventitia.

12. The method of claim 1, wherein:
    a portion of the distal lumen segment adjacent to the target volume is not visible using fluoroscopic techniques before the pressure inside the target volume is reduced; and
    the portion of the distal lumen segment adjacent to the target volume is visible using fluoroscopic techniques after the pressure inside the target volume is reduced.

13. A method for treating a blood vessel including a blood vessel wall defining a blood vessel lumen, the blood vessel lumen being at least partially obstructed by an occlusion, the occlusion dividing the lumen into a proximal lumen segment and a distal lumen segment, the method comprising:
    positioning an orienting element of an orienting catheter inside an intrawall space located distal of the occlusion from the proximal lumen segment, the intrawall space being located between an intima and an adventitia of the blood vessel wall;
    positioning an occluding element of an occlusion catheter in the proximal lumen segment at a location near the occlusion, the occluding element comprising a balloon;
    inflating the balloon of the occlusion catheter in the proximal lumen segment so as to isolate a target volume, the target volume including the intrawall space;

reducing a pressure inside the target volume below a ventral pressure, wherein a pressure inside the intrawall space is greater than a pressure in the distal lumen segment before the pressure inside the target volume is reduced, and the pressure inside the intrawall space is less than the pressure in the distal lumen segment after the pressure inside the target volume is reduced; and advancing a distal end of a reentry device from the orienting element through the intima and into the distal lumen segment while the pressure inside the target volume is below the ventral pressure.

14. The method of claim 13, wherein the pressure inside the target volume is reduced by withdrawing fluid from the target volume.

15. The method of claim 14, wherein the fluid is withdrawn from the target volume through a lumen of the occlusion catheter.

16. The method of claim 14, wherein the fluid is withdrawn from the target volume through a lumen of the orienting catheter.

17. A method for treating a blood vessel including a blood vessel wall defining a blood vessel lumen, the blood vessel lumen being at least partially obstructed by an occlusion, the occlusion dividing the lumen into a proximal lumen segment and a distal lumen segment, the method comprising:

positioning a distal end region of an orienting catheter inside an intrawall space located distal of the occlusion from the proximal lumen segment, the intrawall space being located between an intima and an adventitia of the blood vessel wall;

positioning an occlusion balloon of an occlusion catheter in the proximal lumen segment at a location near the occlusion;

inflating the occlusion balloon of the occlusion catheter in the proximal lumen segment so as to isolate a target volume, the target volume including the intrawall space;

reducing a pressure inside the target volume while the occlusion balloon is inflated in the proximal lumen segment, wherein:

a pressure inside the intrawall space is greater than a pressure in the distal lumen segment before the pressure in the target volume is reduced; and the pressure inside the intrawall space is less than the pressure in the distal lumen segment after the pressure in the target volume is reduced; and advancing a distal end of a reentry device from a port of the orienting catheter through the intima and into the distal lumen segment distal of the occlusion while the distal end region of the orienting catheter is in the intrawall space and the occlusion balloon is inflated in the proximal lumen segment.

18. The method of claim 17, wherein reducing the pressure inside the target volume comprises placing a vacuum source in fluid communication with the target volume via a lumen defined by the orienting catheter or via a lumen defined by the occlusion catheter.

* * * * *